(12) United States Patent
Groarke et al.

(10) Patent No.: US 9,520,574 B2
(45) Date of Patent: Dec. 13, 2016

(54) ELECTROLUMINESCENT DEVICES BASED ON PHOSPHORESCENT IRIDIUM AND RELATED GROUP VIII METAL MULTICYCLIC COMPOUNDS

(75) Inventors: Michelle Groarke, Rowville (AU); Kazunori Ueno, Burwood (AU); Mark Bown, Notting Hill (AU); Sven Andresen, Clayton South (AU)

(73) Assignee: COMMONWEALTH SCIENTIFIC AND INDUSTRIAL RESEARCH ORGANISATION (AU)

( * ) Notice: Subject to any disclaimer, the term of this patent is extended or adjusted under 35 U.S.C. 154(b) by 1009 days.

(21) Appl. No.: 13/643,054

(22) PCT Filed: Apr. 28, 2011

(86) PCT No.: PCT/AU2011/000486
§ 371 (c)(1),
(2), (4) Date: Dec. 17, 2012

(87) PCT Pub. No.: WO2011/134013
PCT Pub. Date: Nov. 3, 2011

(65) Prior Publication Data
US 2013/0082248 A1    Apr. 4, 2013

(30) Foreign Application Priority Data
Apr. 28, 2010   (AU) ................ 2010901797

(51) Int. Cl.
| | |
|---|---|
| H01L 51/54 | (2006.01) |
| C09K 11/06 | (2006.01) |
| H01L 51/50 | (2006.01) |
| C07F 15/00 | (2006.01) |
| H01L 51/00 | (2006.01) |
| H05B 33/10 | (2006.01) |

(52) U.S. Cl.
CPC ....... *H01L 51/5012* (2013.01); *C07F 15/0033* (2013.01); *C09K 11/06* (2013.01); *H01L 51/0085* (2013.01); *H01L 51/5016* (2013.01); *H05B 33/10* (2013.01); *C09K 2211/1007* (2013.01); *C09K 2211/1011* (2013.01); *C09K 2211/1029* (2013.01); *C09K 2211/1037* (2013.01); *C09K 2211/1044* (2013.01); *C09K 2211/1059* (2013.01); *C09K 2211/185* (2013.01)

(58) Field of Classification Search
USPC ......................................................... 540/541
See application file for complete search history.

(56) References Cited

U.S. PATENT DOCUMENTS

| | | | |
|---|---|---|---|
| 4,539,507 | A | 9/1985 | VanSlyke et al. |
| 4,720,432 | A | 1/1988 | VanSlyke et al. |
| 4,885,211 | A | 12/1989 | Tang et al. |
| 6,824,894 | B2 | 11/2004 | Takiguchi et al. |
| 6,830,828 | B2 | 12/2004 | Thompson |
| 2006/0251923 | A1* | 11/2006 | Lin et al. ............ C07F 15/0046 428/690 |
| 2009/0165846 | A1* | 7/2009 | Johannes et al. ... C07F 15/0033 136/256 |

OTHER PUBLICATIONS

International Search Report for corresponding International Patent Application PCT/AU2011/000486 mailed Jul. 5, 2011.
Tang, C.W. et al. "Organic electroluminescent diodes", Applied Physics Letters, vol. 51, 1987, pp. 913-915.
Nonoyama, M. "Benzo[h]quinolin-10-yl-N Iridium(III) Complexes", Bulletin of the Chemical Society of Japan, vol. 47, No. 3, 1974, pp. 767-768.
Lamansky, S. et al. "Synthesis and Characterization of Phosphorescent Cyclometalated Iridium Complexes", Inorg. Chem., vol. 40, 2001, pp. 1704-1711.
Lamansky, S. et al. "Highly Phosphorescent Bis-Cyclometalated Iridium Complexes: Synthesis, Photophysical Characterization, and Use in Organic Light Emitting Diodes", J. Am. Chem. Soc., vol. 123, 2001, pp. 4304-4312.

* cited by examiner

*Primary Examiner* — Marie R. Yamnitzky
(74) *Attorney, Agent, or Firm* — Merchant & Gould P.C.

(57) ABSTRACT

Disclosed herein are phosphorescent materials comprising a complex of a metal atom M selected from Ir, Pt, Rh, Pd, Ru and Os and at least one ligand L, wherein the ligand L is represented by formula (1). Also disclosed are organic electroluminescent devices including such phosphorescent materials.

21 Claims, 2 Drawing Sheets

ELECTROLUMINESCENT DEVICES BASED ON PHOSPHORESCENT IRIDIUM AND RELATED GROUP VIII METAL MULTICYCLIC COMPOUNDS

This application is a National Stage Application of PCT/AU2011/000486, filed 28 Apr. 2011, which claims benefit of Serial No. 2010901797, filed 28 Apr. 2010 in Australia and which applications are incorporated herein by reference. To the extent appropriate, a claim of priority is made to each of the above disclosed applications.

FIELD OF THE INVENTION AND RELATED ART

The present invention relates to novel phosphorescent materials, and to electroluminescent devices containing them.

An organic electroluminescent device is generally comprised of a pair of electrodes forming an anode and a cathode, and one layer or multiple layers comprising a hole transporting layer, emission layer (with an emissive material) and electron transporting layer. Into the organic layer(s), holes and electrons are injected from the anode and the cathode, respectively, thus resulting in excitons within the emission material. When the excitons transition to the ground state, the emissive material emits light.

According to the first study by Eastman Kodak Co. ("Appl. Phys. Lett", vol. 51, pp. 913 (1987), an organic electroluminescent device which comprised a layer of an aluminium quinolinol complex (as electron transporting and luminescent material) and a layer of a triphenylamine derivative (as a hole transporting material) resulted in luminescence of about 1,000 cd/m$^2$ under an application of a voltage of 10 V. Examples of related U.S. Patents include U.S. Pat. Nos. 4,539,507; 4,720,432 and 4,885,211.

The luminescence of such devices may fall into one of two main categories—fluorescence and phosphorescence, based on whether the luminescent material is a fluorescent material or a phosphorescent material. The mechanism through which the luminescence is obtained differs between these categories of materials. Recently, there has been increasing interest in the use of phosphorescent materials in such devices since these materials tend to provide higher quantum yield.

As an example, studies by Baldo et al. revealed a promising (organic light emitting diode) OLED using phosphorescent material as dopant. The quantum yield of the phosphorescent OLED was significantly improved (U.S. Pat. No. 6,830,828). OLED devices comprising both small molecule and polymeric organic materials as components have been reported.

Although in the past twenty years OLEDs have shown significant progress in their performance, there still remain problems that need to be solved. For example, emission material properties can be improved in terms of the tunability of the light that the OLED can emit. Thus, there is an ongoing interest in developing new phosphorescent materials with new or improved properties.

SUMMARY OF THE INVENTION

The present invention provides a new range of phosphorescent materials. The present invention also provides new organic electroluminescent devices containing such phosphorescent materials.

According to a first aspect, there is provided an organic electroluminescent device comprising:
a pair of electrodes comprising an anode and a cathode, and
one or more layers of organic compound arranged between the pair of electrodes, wherein the organic compound layer, or one or more of the organic compound layers, comprises a phosphorescent material;
wherein the phosphorescent material comprises a complex of a metal atom M selected from Ir, Pt, Rh, Pd, Ru and Os and at least one ligand L, wherein the ligand L is represented by formula (1):

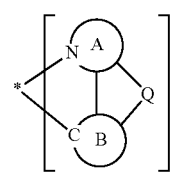

(1)

wherein:
ring A is a 5-membered heterocycle which is unsubstituted or substituted by one or more substituents, containing at least one nitrogen atom as represented in formula (1), which is bound to the metal atom at the asterisk (*),
ring B is a 5- or 6-membered carbocycle or heterocycle which is unsubstituted or substituted by one or more substituents, containing a carbon atom as represented in formula (1) which is bound to the metal atom at the asterisk (*),
rings A and B are joined by a direct covalent bond as represented in formula (1),
rings A and B are joined via a tether Q, wherein
Q is a linear, branched or cyclic alkyl, aryl or alkyl-aryl tether of between 3 and 20 carbon atoms in length, wherein one or more of the carbon atoms in the tether may be replaced with —O—, —S—, —CO—, —CO$_2$—, —CH=CH—, —NH—, —CONH—, —C=N—, —Si— and —P—, wherein the atoms —Si— and —P— contain substituents based on their valency, and wherein any carbon, nitrogen, silicon or phosphorous atom of the tether may contain one or more substituents selected from the group consisting of halogen, cyano, amide, imine, imide, amidine, amine, nitro, hydroxy, ether, carbonyl, carboxy, carbonate, carbamate, phosphine, phosphate, phosphonate, sulphide, sulphone, sulphoxide, alkenyl, aryl, alkyl, heteroaryl, alkynyl, silyl, and substituents containing a functional group that can be polymerised or a polymer chain, or two substituents may together form a ring or fused ring system.

The phosphorescent material can be used as an emission material in the organic electroluminescent device. The phosphorescent material may form a layer of the device, or a component of a layer of the device. For example, the phosphorescent material may be present as a dopant within a host material, wherein the host material may be an electron transporting material or a hole transporting material or both.

The possible substituents in rings A and B of the phosphorescent material used in the device may independently be selected from the group consisting of:
halogen, cyano, amide, imine, imide, amidine, amine, nitro, hydroxy, ether, carbonyl, carboxy, carbonate, carbamate, phosphine, phosphate, phosphonate, sulphide, sulphone, sulphoxide, alkenyl, alkynyl, silyl, and substituents containing a functional group that can be polymerised or a polymer chain, and substituted or unsubstituted alkyl, substituted or unsubstituted aryl and substituted or unsubstituted alkyl-aryl wherein:

one or more of the carbon atoms in the alkyl, aryl or alkyl-aryl may be replaced with an atom or group selected from the group consisting of: —O—, —S—, —CO—, —CO$_2$—, —CH═CH—, —CONH—, —C═N—, —NH—, —Si— and —P— (wherein the atoms —Si— and —P— contain substituents for neutrality based on their valency), the substituents on the alkyl, aryl or alkyl-aryl are selected from the group consisting of: halogen, cyano, amide, imine, imide, amidine, amine, nitro, hydroxy, ether, carbonyl, carboxy, carbonate, carbamate, phosphine, phosphate, phosphonate, sulphide, sulphone, sulphoxide, alkenyl, alkynyl, silyl, and substituents containing a functional group that can be polymerised or a polymer chain, and the alkyl, aryl or alkyl-aryl may additionally be connected to the tether Q, or the alkyl, aryl or alkyl-aryl may be attached via two points to its core ring (A or B) to form a fused ring or ring system.

According to a second aspect, there is provided an organic electroluminescent device comprising:

a pair of electrodes comprising an anode and a cathode, and one or more layers of organic compound arranged between the pair of electrodes, wherein the organic compound layer, or one or more of the organic compound layers, comprises a phosphorescent material;

wherein the phosphorescent material has a formula (2):

$$ML_mL'_n \qquad (2)$$

wherein:
M is a metal atom selected from Ir, Pt, Rh, Pd, Ru and Os,
L is a ligand represented by formula (1), as defined above,
L' is a bidentate ligand of a different identity to L,
m is an integer selected from 1, 2 and 3, and
n is an integer selected from 0, 1 and 2.

According to a third aspect, there is provided a phosphorescent material comprising a complex of a metal atom M selected from Ir, Pt, Rh, Pd, Ru and Os and at least one ligand L, wherein the ligand L is represented by formula (1), as defined above.

According to a fourth aspect, there is provided a phosphorescent material of formula (2):

$$ML_mL'_n \qquad (2)$$

wherein:
M is a metal atom selected from Ir, Pt, Rh, Pd, Ru and Os,
L is a ligand represented by formula (1), as defined above,
L' is a bidentate ligand of a different identity to L,
m is an integer selected from 1, 2 and 3, and
n is an integer selected from 0, 1 and 2.

According to a fifth aspect, there is provided a method for the production of a phosphorescent material comprising:

reacting a precursor complex of a metal M, with a ligand L, in a ratio suitable to result in a product containing the desired number of ligands L being co-ordinated to the metal M, optionally followed by:

reacting the product with another ligand L' in a ratio suitable to introduce the desired number of ligands L' into the product, wherein:
M is a metal atom selected from Ir, Pt, Rh, Pd, Ru and Os,
L is a ligand represented by formula (1), as defined above, and
L' is a bidentate ligand of a different identity to L.

According to a sixth aspect, there is provided an organic electroluminescent device comprising the phosphorescent material of the third or fourth aspect.

According to a seventh aspect, there is also provided the use of a phosphorescent material of the third or fourth aspect in an organic electroluminescent device.

According to an eighth aspect, there is also provided the use of a phosphorescent material of the third or fourth aspect as an emission material in an organic electroluminescent device.

DETAILED DESCRIPTION OF THE PREFERRED EMBODIMENTS

Figure 1:
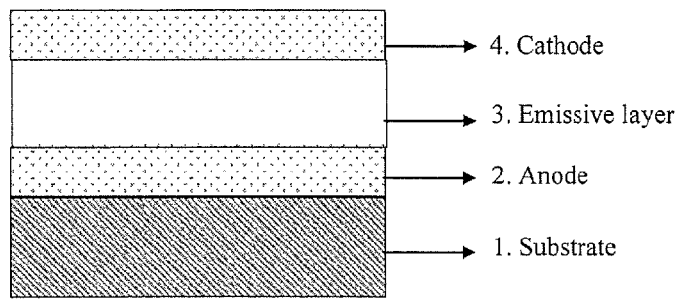
FIG. 1 is a schematic illustration of the basic structure of an organic electroluminescent device according to a first embodiment of the invention.

The phosphorescent material for use in the organic electroluminescent device of the present application comprises a complex of a metal atom M selected from Ir, Pt, Rh, Pd, Ru, and Os and at least one ligand L of formula (1).

The phosphorescent material may, in some embodiments be homoleptic (i.e. containing the same ligands that fall within the scope of the ligand L represented by formula (1)).

In alternative embodiments, the phosphorescent material may be heteroleptic (i.e. containing different ligands falling within the scope of the ligand L represented by formula (1), or containing at least one ligand falling within the scope of the ligand L represented by formula (1) and other ligands (e.g. bidentate ligands L' having the formula (5), (6) or (7) set out below)).

The term "material" in the expression "phosphorescent material" is used in its broadest sense to refer to any chemical substance containing the required metal and ligand of formula (1), and extends to compounds, complexes, polymers, monomers and the like materials. It will be understood that some forms of the phosphorescent material are polymer forms. The reference to the material being "phosphorescent" indicates that the material has the property of being capable of emitting light following excitation, through transitioning of the excitons to ground state. This is typically from a triplet exciton state.

The phosphorescent material may be referred to as a phosphorescent complex, or a phosphorescent organometallic complex.

According to some embodiments, the metal atom is Ir. Such phosphorescent materials containing Ir as the metal atom may be referred to as phosphorescent iridium complexes.

In the case of phosphorescent iridium complexes, iridium tends to form a hexa-coordinate complex with the subject ligands. The ligand of formula (1) coordinates to the iridium at two coordination sites. The phosphorescent material may comprise up to 3 ligands L of formula (1), or may comprise one or two ligands of formula (1), and one or more additional ligands.

In the case where the metal atom is hexa-coordinate, and all of the ligands of the complex are bidentate, the phosphorescent material may comprises 3 bidentate ligands, specifically between one and three ligands L of formula (1), and 0, 1 or 2 further ligands L'.

The phosphorescent material may be of formula (2):

$$ML_mL'_n \quad (2)$$

wherein M and L are as defined previously, L' is a bidentate ligand of a different identity to L, m is an integer selected from 1, 2 and 3, and n is an integer selected from 0, 1 and 2.

Where the metal atoms are hexa-coordinate, such as in the case of Ir, Ru, Rh or Os, m+n=3.

Details of the further ligands L' that may be present in the phosphorescent material are set out below.

In the case of some of the metal atoms, such as Pt or Pd, the phosphorescent material may comprise 1 or 2 ligands L of formula (1), and 0 or 1 additional bidentate ligands. Thus, for these metal atoms, in formula (2), m+n=2.

Ring A

The ligand L represented by formula (1) contains an A ring which is a 5-membered aromatic or non-aromatic heterocycle containing at least one nitrogen atom, wherein the nitrogen atom can bind (or is bound) to the metal atom. The other 4 atoms in the A ring may be selected from carbon (containing H or a substituent), nitrogen (optionally containing H or a substituent), oxygen and sulphur atoms.

Examples of A rings encompassed in the present application are as follows:
rings containing N and C, such as pyrazoles, pyrazolines, imidazoles, imidazolines, triazoles, tetrazoles;
rings containing N, C and O, such as oxazoles oxazolines, oxadiazoles;
rings containing N, C and S, such as thiazoles, thiazolines, thiadiazoles;
and their fused derivatives. Some of these rings are illustrated by, but not restricted to, the examples below:

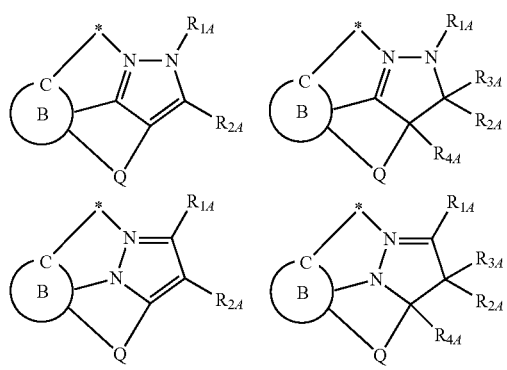

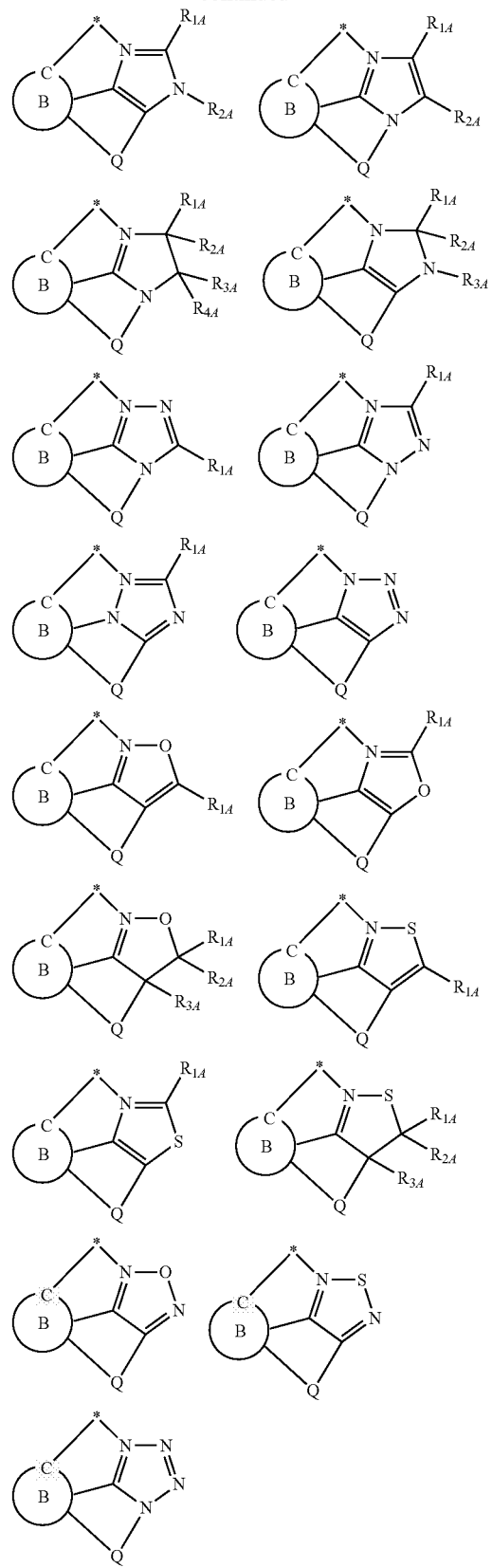

According to one embodiment, the 4 atoms other than the nitrogen atom illustrated in Formula (1) in the A ring are carbon or nitrogen, wherein the carbon atoms contain H or a substituent and the nitrogen atoms may contain H or a substituent.

Possible substituents on the atoms in the A ring (e.g., the substituents $R_{1A}$ to $R_{4A}$ shown in the examples of ring A depicted above) can be selected from the group consisting of:

halogen, cyano, amide, imine, imide, amidine, amine, nitro, hydroxy, ether, carbonyl, carboxy, carbonate, carbamate, phosphine, phosphate, phosphonate, sulphide, sulphone, sulphoxide, alkenyl, alkynyl, silyl, and substituents containing a functional group that can be polymerised or a polymer chain, and substituted or unsubstituted alkyl, substituted or unsubstituted aryl and substituted or unsubstituted alkyl-aryl, wherein:

one or more of the carbon atoms in the alkyl, aryl or alkyl-aryl may be replaced with an atom or group selected from the group consisting of: —O—, —S—, —CO—, —CO$_2$—, —CH═CH—, —C≡C—, —NH—, —CONH—, —C═N—, —Si— and —P— (wherein the atoms —Si— and —P— contain substituents for neutrality based on their valency), the substituents on the alkyl, aryl or alkyl-aryl are selected from the group consisting of: halogen, cyano, amide, imine, imide, amidine, amine, nitro, hydroxy, ether, carbonyl, carboxy, carbonate, carbamate, phosphine, phosphate, phosphonate, sulphide, sulphone, sulphoxide, alkenyl, alkynyl, silyl and substituents containing a functional group that can be polymerised or a polymer chain, and the alkyl, aryl or alkyl-aryl may additionally be connected to the tether Q, or the alkyl, aryl or alkyl-aryl may be attached via two points to ring A to form a fused ring or ring system.

Ring B

The ligand L represented by formula (1) contains a B ring which is a 5-membered or 6-membered aromatic or non-aromatic carbocycle or heterocycle containing a carbon atom which is (or can be) bound to the metal atom (as illustrated in formula (1)).

The other 4 or 5 atoms in the B ring are selected from carbon (containing H or a substituent), nitrogen (which may be substituted or unsubstituted), oxygen and sulphur atoms. As some examples, the B ring may be selected from the group consisting of: rings containing only C, such as: benzene, cyclohexene, cyclohexadiene, cyclopentene and cyclopentadiene;

rings containing N and C, such as: pyridine, pyridazines, pyrimidines, pyrroles, pyrazoles, dihydropyridines, dihydropridazines, dihydropyrimidines, pyrroline, pyrazolines;

rings containing O and C, such as: pyranes, dioxins, furanes, dihydropyranes, dihydrofuranes;

rings containing S and C, such as: thiophenes, dihydrothiophenes;

rings containing N, C and O, such as: oxazines, oxazoles, dihydrooxazines;

rings containing S, C and O, such as: oxathiazines, dihydrooxathiazine;

rings containing N, C and S, such as: thiazoles;

rings containing N, C, O and S, such as: oxathiazoles;

and their fused derivatives.

Some possible ring structures for ring B are illustrated by, but not restricted to, the examples below:

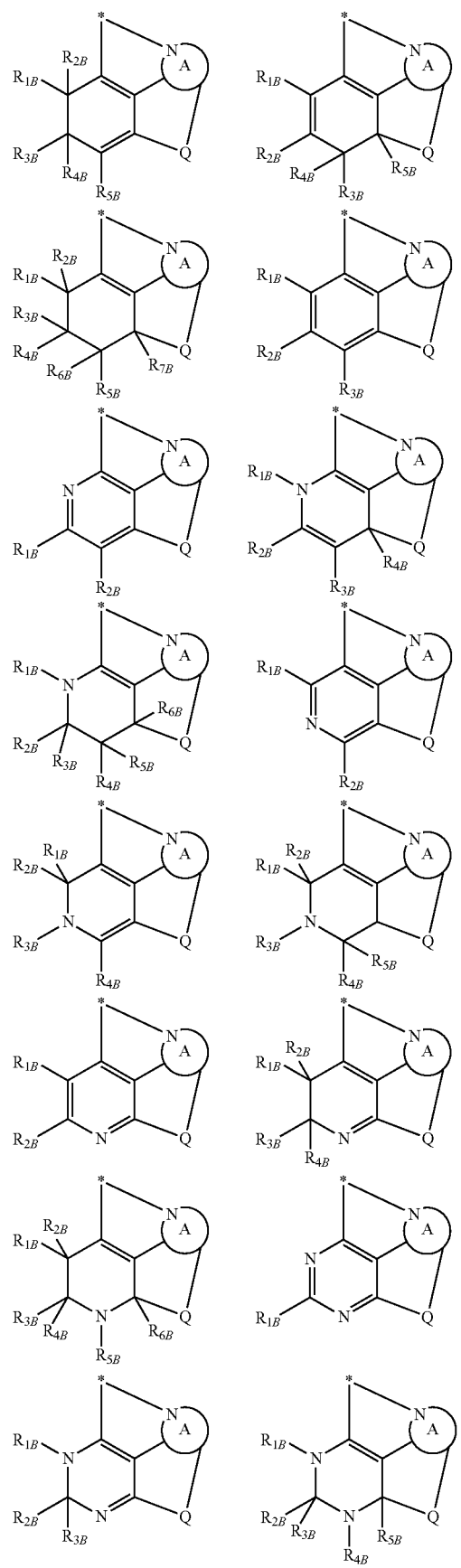

-continued
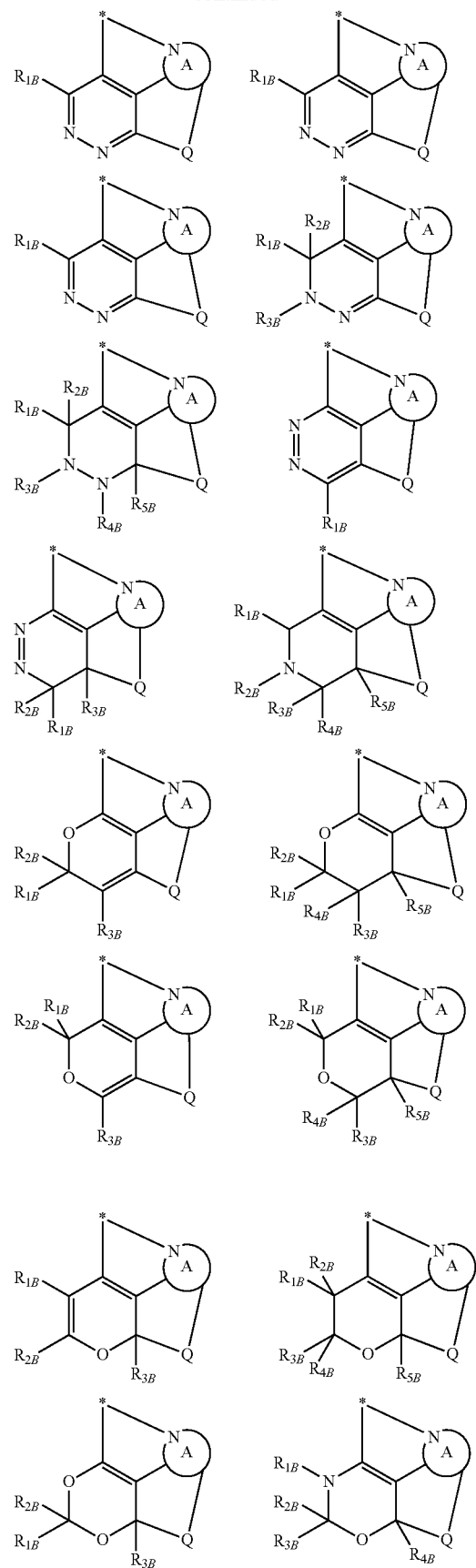
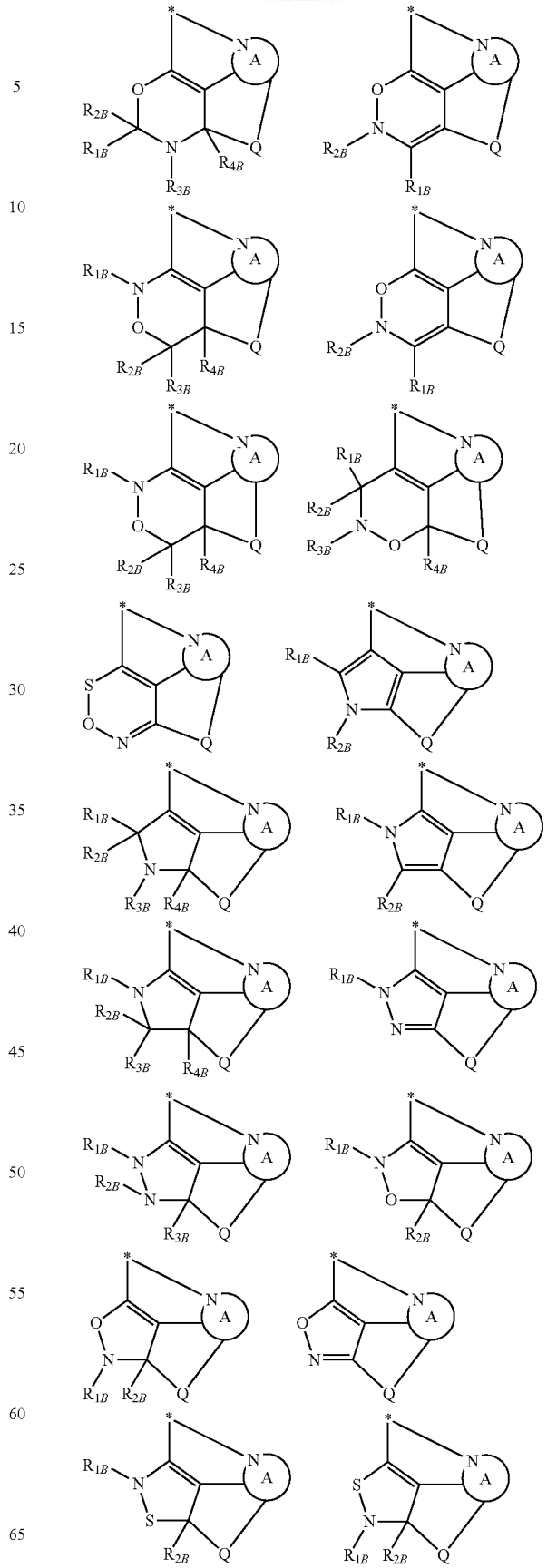

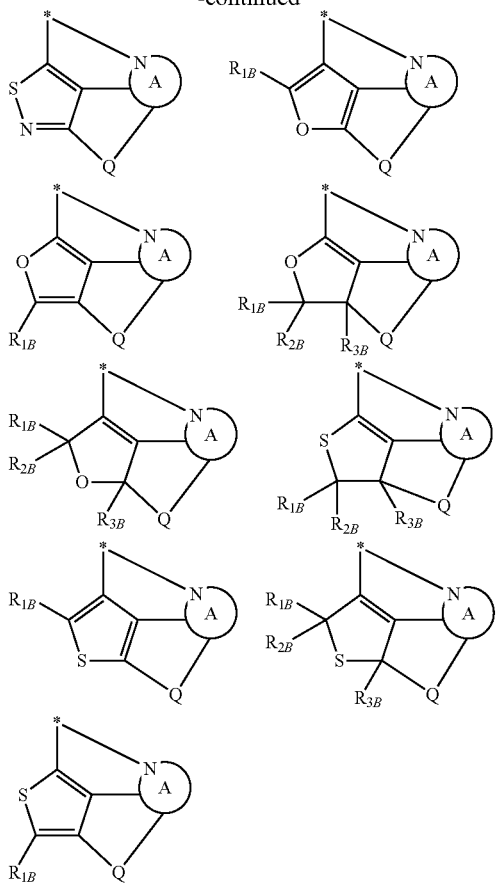

According to one embodiment, the 4 or 5 atoms other than the illustrated carbon atom in the B ring are each carbon, nitrogen or sulphur.

Possible substituents on the atoms in the B ring (e.g., the substituents $R_{1B}$ to $R_{6B}$ shown in the examples of ring B depicted above) can be selected from the group consisting of:

halogen, cyano, amide, imine, imide, amidine, amine, nitro, hydroxy, ether, carbonyl, carboxy, carbonate, carbamate, phosphine, phosphate, phosphonate, sulphide, sulphone, sulphoxide, alkenyl, alkynyl, silyl, and substituents containing a functional group that can be polymerised or a polymer chain, and substituted or unsubstituted alkyl, substituted or unsubstituted aryl and substituted or unsubstituted alkyl-aryl, wherein:

one or more of the carbon atoms in the alkyl, aryl or alkyl-aryl may be replaced with an atom or group selected from the group consisting of: —O—, —S—, —CO—, —CO$_2$—, —CH═CH—, —C≡C—, —NH—, —CONH—, —C═N—, —Si— and —P— (wherein the atoms —Si— and —P— contain substituents based on their valency), the substituents on the alkyl, aryl or alkyl-aryl are selected from the group consisting of: halogen, cyano, amide, imine, imide, amidine, amine, nitro, hydroxy, ether, carbonyl, carboxy, carbonate, carbamate, phosphine, phosphate, phosphonate, sulphide, sulphone, sulphoxide, alkenyl, alkynyl, silyl and substituents containing a functional group that can be polymerised or a polymer chain, and the alkyl, aryl or alkyl-aryl may additionally be connected to the tether Q, or the alkyl, aryl or alkyl-aryl may be attached via two points to ring B to form a fused ring or ring system.

Rings A and B are joined by a direct covalent bond as represented in formula (1).

Rings A and B are also joined via a tether Q.

Tether Q

Q is a linear, branched or cyclic alkyl, aryl or alkyl-aryl tether of between 3 and 20 carbon atoms in length, wherein:

one or more of the carbon atoms in the tether may be replaced with —O—, —S—, —CO—, —CO$_2$—, —CH═CH—, —C≡C—, —NH—, —CONH—, —C═N—, —Si— and —P— (wherein the atoms —Si— and —P— contain substituents based on their valency), any carbon, nitrogen, silicon or phosphorous atom of the tether may contain one or more substituents (e.g., those depicted below as $R_{1Q}$ to $R_{6Q}$) selected from the group consisting of halogen, cyano, amide, imine, imide, amidine, amine, nitro, hydroxy, ether, carbonyl, carboxy, carbonate, carbamate, phosphine, phosphate, phosphonate, sulphide, sulphone, sulphoxide, alkenyl, aryl, alkyl, heteroaryl, alkynyl, silyl, and substituents containing a functional group that can be polymerised or a polymer chain, or two substituents may together form a ring or fused ring system. The ring or fused ring system may optionally be attached or fused to one or both of rings A and B.

Examples of suitable tethers Q include, but are not restricted to, the following:

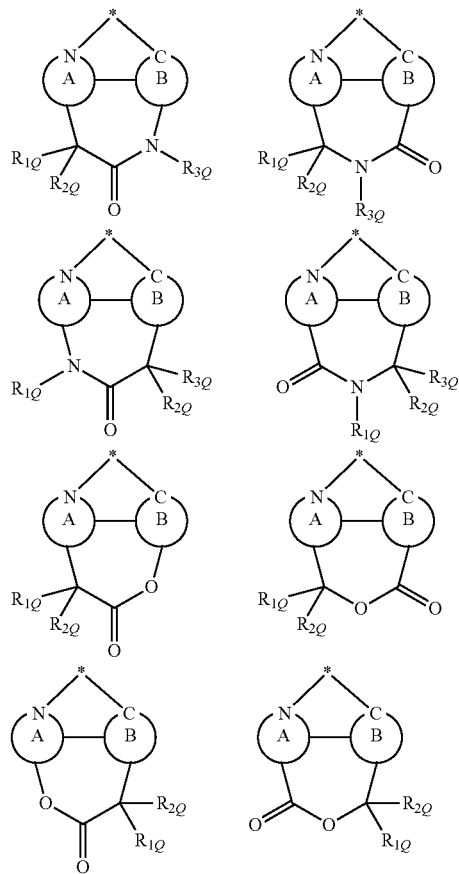

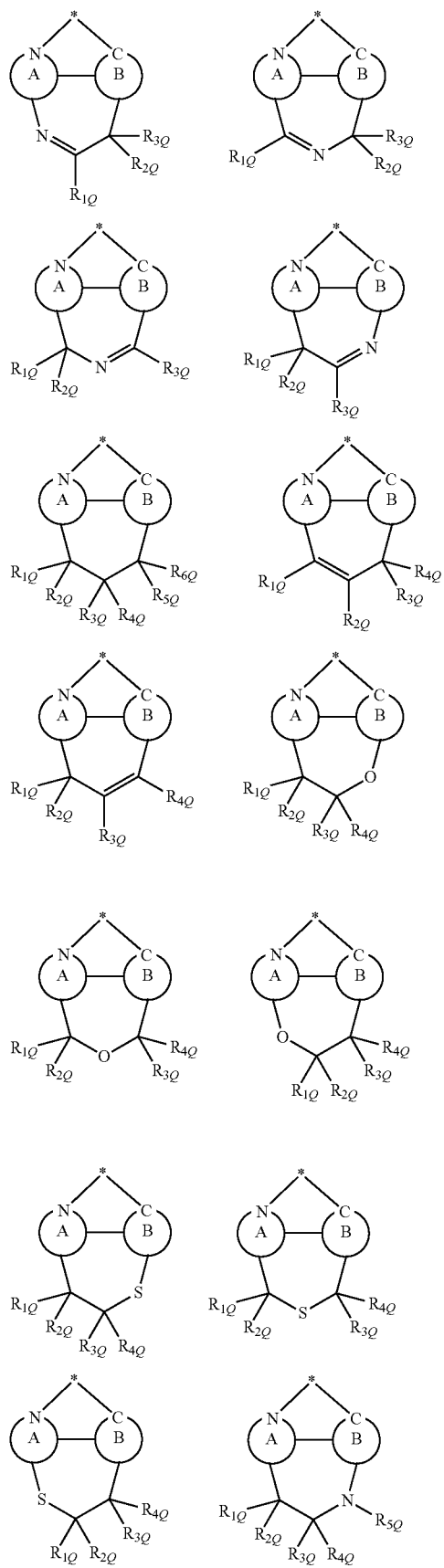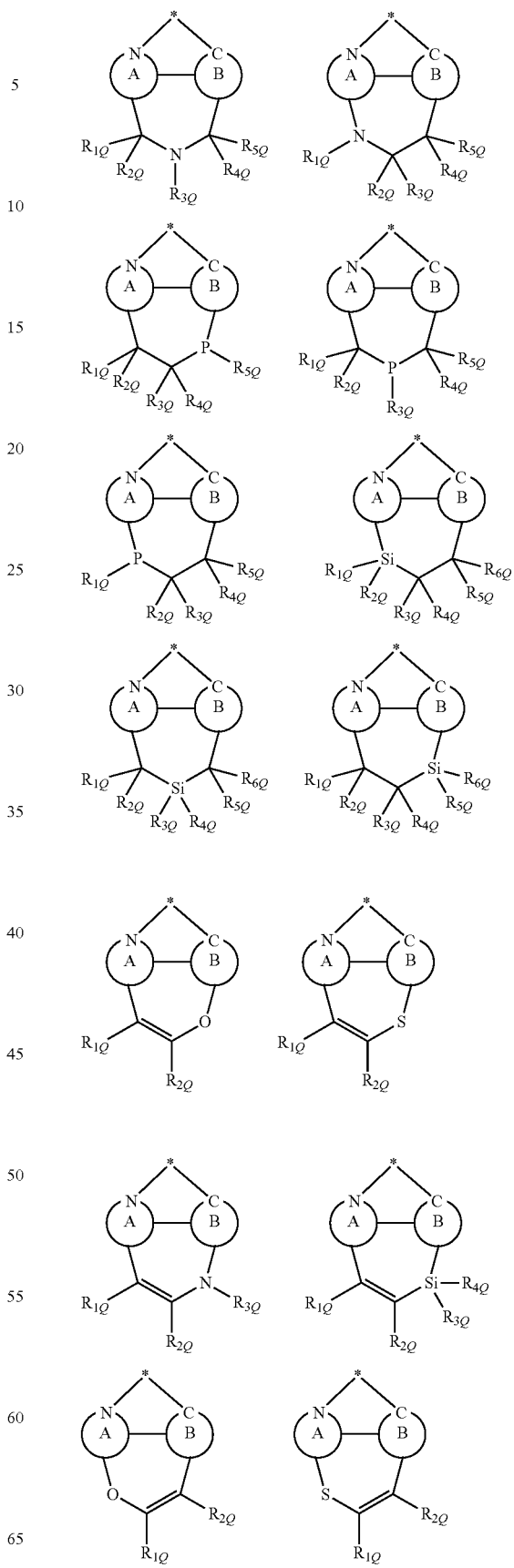

-continued

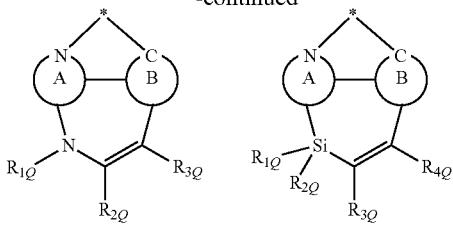

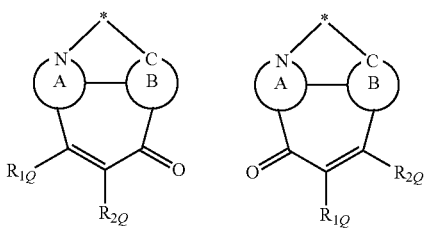

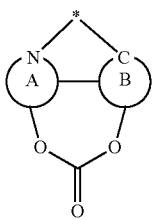

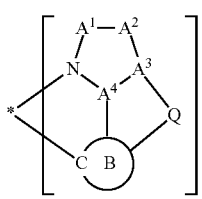

It will be noted that the tether is of at least 3 carbon atoms in length. When combined with the atoms from the A and B rings, this results in the formation of a minimum 7-membered ring. A tether of 4 atoms in length (being carbon, or substitutes for carbon) forms an 8-membered ring, and so forth for increasing tether lengths.

Specific Embodiments of Ligand L

According to one embodiment, the ligand L is of the formula (3):

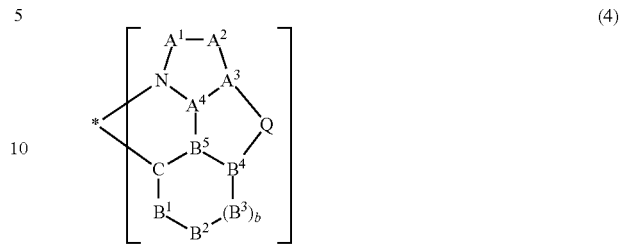

(3)

wherein Q and ring B are as defined previously, and wherein:

$A^1$ and $A^2$ are each independently selected from the group consisting of: C, N, O and S, wherein the C or N may be substituted or unsubstituted, $A^3$ and $A^4$ are selected from the group consisting of: C and N, wherein the C may be substituted or unsubstituted.

According to one embodiment, the ligand L is of formula (4):

$$\begin{bmatrix} \text{(structure)} \end{bmatrix} \quad (4)$$

wherein Q is as defined previously, and wherein:

$A^1$ and $A^2$ are each independently selected from the group consisting of: C, N, O and S, wherein the C or N may be substituted or unsubstituted, $A^3$ and $A^4$ are selected from the group consisting of: C and N, wherein the C may be substituted or unsubstituted, $B^1$ and $B^2$ are each independently selected from the group consisting of: C, N, O and S, wherein the C or N may be substituted or unsubstituted, $B^3$, when present, is selected from the group consisting of: C, N, O and S, wherein the C or N may be substituted or unsubstituted, b is 0 or 1, $B^4$ is selected from the group consisting of: C and N, wherein the C may be substituted or unsubstituted, and $B^5$ is C.

The optional substituents on $A^1$, $A^2$, $B^1$, $B^2$ and $B^3$ (when present) are as described previously for the optional ring substituents for rings A and B.

According to some embodiments, $A^1$ and $A^2$ are C or N, wherein the C or N is unsubstituted or substituted. According to some embodiments, $B^1$, $B^2$ and $B^3$ (when present) are selected from C, N or S, wherein the C or N is unsubstituted or substituted.

Examples of suitable ligands L include, but are not restricted to, the following:

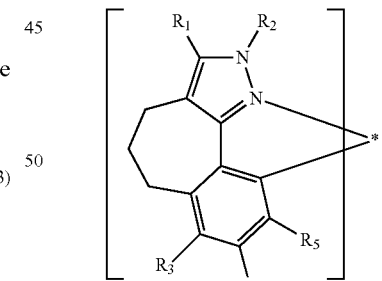

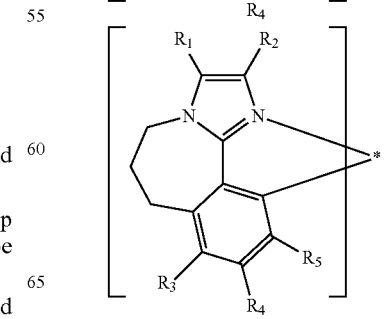

-continued
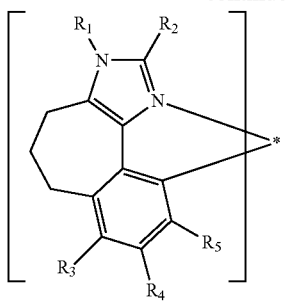
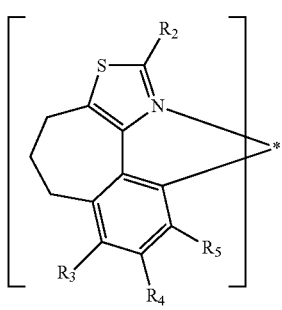
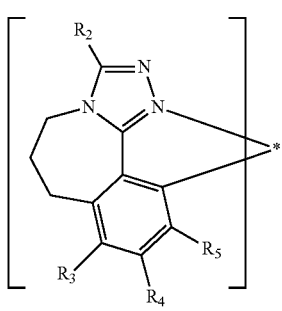
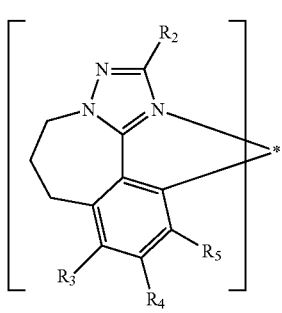
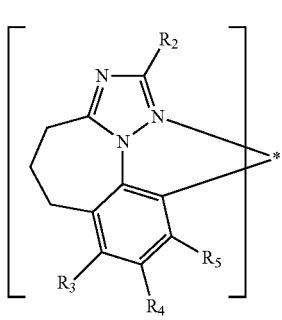
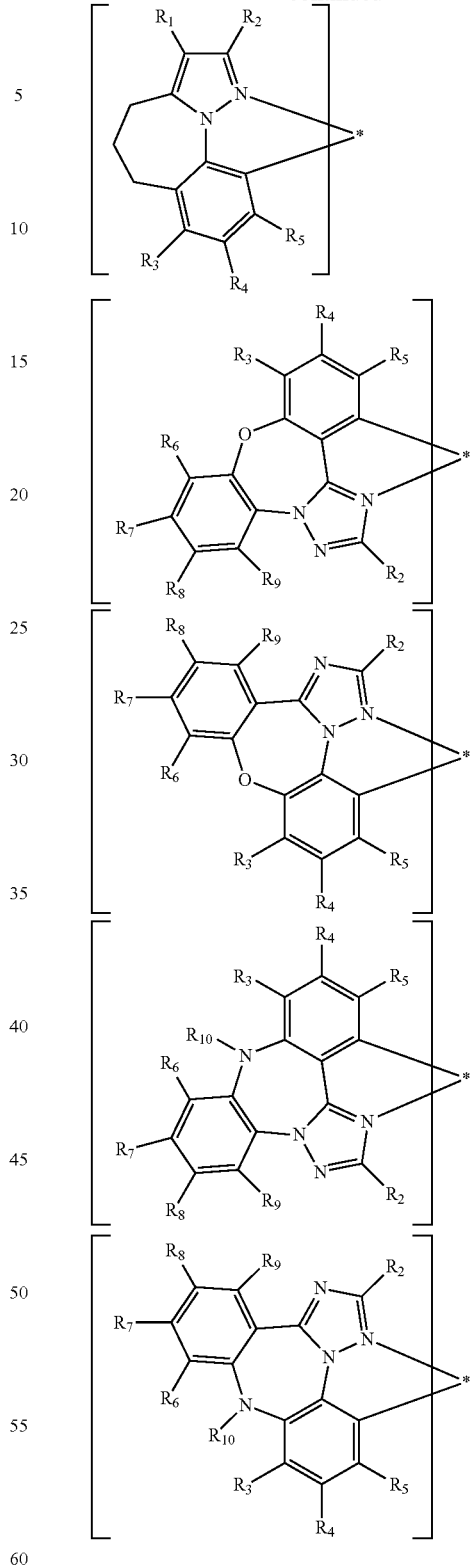
wherein:
$R_1$, $R_2$, $R_3$, $R_4$, $R_5$, $R_6$, $R_7$, $R_8$, $R_9$ and $R_{10}$ can be independently selected from the group consisting of:
halogen, cyano, amide, imine, imide, amidine, amine, nitro, hydroxy, ether, carbonyl, carboxy, carbonate, carbamate, phosphine, phosphate, phosphonate, sulphide, sulphone, sulphoxide, alkenyl, alkynyl, silyl, and substituents containing a functional group that can be polymerised or a polymer chain, and substituted or unsubstituted alkyl, substituted or unsubstituted aryl and substituted or unsubstituted alkyl-aryl, wherein:

one or more of the carbon atoms in the alkyl, aryl or alkyl-aryl may be replaced with an atom or group selected from the group consisting of: O, —S—, —CO—, —CO$_2$—, —CH═CH—, —C≡C—, —NH—, —CONH—, —C═N—, —Si— and —P— (wherein the atoms —Si— and —P— contain substituents based on their valency), the substituents on the alkyl, aryl or alkyl-aryl are selected from the group consisting of: halogen, cyano, amide, imine, imide, amidine, amine, nitro, hydroxy, ether, carbonyl, carboxy, carbonate, carbamate, phosphine, phosphate, phosphonate, sulphide, sulphone, sulphoxide, alkenyl, alkynyl, silyl and substituents containing a functional group that can be polymerised or a polymer chain.

Further Ligands L'

In general, any ligands known in the art may be used as the further ligands that may be complexed with the metal atom, when the number of ligands L of formula (1) are not sufficient to fill all co-ordination sites for the metal atom. These may be monodentate, or multidentate, such as bidentate, tridentate, tetradentate or so forth. Bidentate ligands are preferred.

According to some embodiments, the further ligands L' are bidentate. Some examples are those of formulae (5), (6) and (7) set out below:

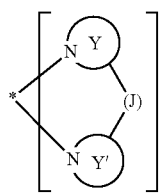

(5)

wherein:

ring Y is a 5-, 6- or 7-membered heterocycle which is unsubstituted or substituted by one or more substituents, containing at least one nitrogen atom as represented in the formula, which can bind to the metal atom at the asterisk (*), ring Y' is a 5-, 6- or 7-membered heterocycle which is unsubstituted or substituted by one or more substituents, and containing at least one nitrogen atom as represented in the formula which can bind to the metal atom at the asterisk (*), and rings Y and Y' are either joined by a direct covalent bond or via a linker J as represented in formula (5), wherein J, when present, is a B, C, O, N, P, Si or S atom which is covalently bonded to both rings Y and Y' and which may be substituted or unsubstituted depending on its valency;

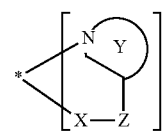

(6)

wherein:

ring Y is as defined previously,

Z is a ligand component connected via a covalent bond to ring Y, and connected to the metal atom via X, and X is an N, O, S or P atom which can bind to the metal M at the asterisk (*), wherein the N or P atom is unsubstituted or is substituted;

(7)

wherein:

G is a ligand component comprising one or two substituted or unsubstituted carbon atoms, which is connected covalently to two O-atoms, and the O atoms can each bind to the metal M at the asterisk (*).

Y and Y'

Each of Y and Y', for each of formulae (5) and (6), are independently selected from 5-, 6- or 7-membered heterocycles which are unsubstituted or substituted by one or more substituents. Y and Y' contain at least one nitrogen atom as represented in formula (5) and formula (6).

The other 4, 5 or 6 atoms in the Y and Y' rings are selected from carbon (containing H or a substituent), nitrogen (which may be substituted or unsubstituted), oxygen, sulphur and silicon (which may be substituted or unsubstituted) atoms.

As some examples, the Y and Y' rings (which contain at least one nitrogen atom) may be selected from the group consisting of:

rings containing N and C, such as: pyrazoles, pyrazolines, imidazoles, imidazolines, triazoles, tetrazoles, pyrrolidines, pyrrolines, pyrrols, imidazolidines, pyrazolidines, piperidines, pyridines, dihydropyridines, pipirazines, dihydropyrazines, pyrazines, pyridazines, dihydropyridazines, dihydropyrimidines, pyrimidines, dihydrotriazines, triazines, azepines, dihydroazepines, tetrahydroazepines, azepanes, diazepines, dihydrodiazepines, tetrahydrodiazepanes, diazepanes;

rings containing N, C and O, such as: oxazoles oxazolines, oxadiazoles, dioxazoles, oxatriazoles, morpholines, oxazines, dihydrooxazines, oxadiazines, dihydrooxadiazines;

rings containing N, C and S, such as: thiazoles, thiazolines, thiadiazoles, thiomorpholines, thiazines, dihydrothiazines;

rings containing N, C, O and S, such as: oxathiazoles;

and their fused derivatives;

and sila-containing variants of the above rings.

The possible substituents on the atoms in the Y and Y' rings can be independently selected from the group consisting of:

halogen, cyano, amide, imine, imide, amidine, amine, nitro, hydroxy, ether, carbonyl, carboxy, carbonate, carbamate, phosphine, phosphate, phosphonate, sulphide, sulphone, sulphoxide, alkenyl, alkynyl, silyl, and substituents containing a functional group that can be polymerised or a polymer chain, and substituted or unsubstituted alkyl, substituted or unsubstituted aryl and substituted or unsubstituted alkyl-aryl, wherein:

one or more of the carbon atoms in the alkyl, aryl or alkyl-aryl may be replaced with an atom or group selected from the group consisting of: O, —S—, —CO—, —CO$_2$—, —CH=CH—, —C≡C—, —NH—, CONH, —C=N—, —Si— and —P— (wherein the atoms —Si— and —P— contain substituents based on their valency), the substituents on the alkyl, aryl or alkyl-aryl are selected from the group consisting of: halogen, cyano, amide, imine, imide, amidine, amine, nitro, hydroxy, ether, carbonyl, carboxy, carbonate, carbamate, phosphine, phosphate, phosphonate, sulphide, sulphone, sulphoxide, alkenyl, alkynyl, silyl and substituents containing a functional group that can be polymerised or a polymer chain, and the alkyl, aryl or alkyl-aryl may additionally be connected to another ring of the ligand, or the alkyl, aryl or alkyl-aryl may be attached via two points to the subject ring to form a fused ring or ring system.

Ligand Component J

J, when present, is chosen from B, C, O, N, P, Si, S, which may be substituted or unsubstituted depending on its valency. Such substituents may independently be chosen from:

a linear, branched or cyclic alkyl, aryl or alkyl-aryl group of between 1 and 20 carbon atoms in length, wherein one or more of the carbon atoms in the linear, branched or cyclic alkyl, aryl or alkyl-aryl group may be replaced with O, —S—, —CO—, —CO$_2$—, —CH=CH—, —C≡C—, —NH—, —CONH—, —C=N—, and wherein any carbon or nitrogen atom of the linear, branched or cyclic alkyl, aryl or alkyl-aryl group may contain one or more substituents selected from the group consisting of halogen, cyano, amide, imine, imide, amidine, amine, nitro, hydroxy, ether, carbonyl, carboxy, carbonate, carbamate, phosphine, phosphate, phosphonate, sulphide, sulphone, sulphoxide, alkenyl, aryl, alkyl, heteroaryl, alkynyl, silyl, and substituents containing a functional group that can be polymerised or a polymer chain, or two substituents may together form a ring or fused ring system; or 5-, 6- and 7-membered carbocycles or heterocycles, which may themselves be unsubstituted or substituted.

Examples of 5- 6- and 7-membered carbocycles or heterocycles include: rings containing C, such as: benzenes;

rings containing N and C, such as: pyrrolidines, pyrrolines, pyrrols, imidazolidines, imidazolines, imidazoles, pyrazolidines, pyrazolines, pyrazoles, triazoles, tetrazoles, piperidines, pyridines, dihydropyridines, pipirazines, dihydropyrazines, pyrazines, pyridazines, dihydropyridazines, dihydropyrimidines, pyrimidines, dihydrotriazines, triazines, azepines, dihydroazepines, tetrahydroazepines, azepanes, diazepines, dihydrodiazepines, tetrahydrodiazepanes, diazepanes;

rings containing N, C and O, such as: oxazolines, oxazoles, oxadiazoles, dioxazoles, oxatriazoles, morpholines, oxazines, dihydrooxazines, oxadiazines, dihydrooxadiazines; rings containing N, C and S, such as: thiazolines, thiazoles, thiadiazoles; rings containing N, C, O and S, such as: oxathiazoles, thiomorpholines, thiazines, dihydrothiazines; and sila-containing variants of the above rings Ligand Component Z Z is a ligand component connected via a covalent bond to ring Y, and connected to the metal atom via X.

In the context of ligand component Z, the term "ligand component" refers to any group or moiety that may be located between ring Y and the atom X through which the ligand is attached to the metal atom. As an example, the ligand component may be selected from:

a linear, branched or cyclic alkyl, aryl or alkyl-aryl group of between 1 and 20 carbon atoms in length, wherein: one or more of the carbon atoms in the ligand component may by replaced with —O—, —S—, —CO—, —CO$_2$—, —CH=CH—, —C≡C—, —NH—, —CONH—, —C=N—, —Si— and —B— (wherein the —Si— and —B— contain substituents based on their valency), and wherein any carbon, nitrogen, silicon or boron atom of the ligand component may contain one or more substituents selected from the group consisting of halogen, cyano, amide, imine, imide, amidine, amine, nitro, hydroxy, ether, carbonyl, carboxy, carbonate, carbamate, phosphine, phosphate, phosphonate, sulphide, sulphone, sulphoxide, alkenyl, aryl, alkyl, heteroaryl, alkynyl, silyl, and substituents containing a functional group that can be polymerised or a polymer chain, or two substituents may together form a ring or fused ring system; or 5- 6- and 7-membered carbocycles or heterocycles, which may be unsubstituted or substituted.

Examples of 5- 6- and 7-membered carbocycles or heterocycles include:

rings containing C, such as: benzenes;

rings containing N and C, such as: pyrrolidines, pyrrolines, pyrrols, imidazolidines, imidazolines, imidazoles, pyrazolidines, pyrazolines, pyrazoles, triazoles, tetrazoles, piperidines, pyridines, dihydropyridines, pipirazines, dihydropyrazines, pyrazines, pyridazines, dihydropyridazines, dihydropyrimidines, pyrimidines, dihydrotriazines, triazines, azepines, dihydroazepines, tetrahydroazepines, azepanes, diazepines, dihydrodiazepines, tetrahydrodiazepanes, diazepanes;

rings containing N, C and O, such as: oxazolines, oxazoles, oxadiazoles, dioxazoles, oxatriazoles, morpholines, oxazines, dihydrooxazines, oxadiazines, dihydrooxadiazines;

rings containing N, C and S, such as: thiazolines, thiazoles, thiadiazoles;

rings containing N, C, O and S, such as: oxathiazoles, thiomorpholines, thiazines, dihydrothiazines; and sila-containing variants of the above rings Ligand Component X X is selected from: N, O, S or P atoms. X forms a monovalent bond with the metal M at the asterisk (*).

When atom X is N or P, the N and P atoms may contain one or more substituents selected from the group consisting of: alkyl, aryl, alkyl-aryl (wherein one or more of the carbon atoms in the alkyl, aryl, alkyl-aryl may be replaced with N, O, S, P or Si, said replacement atoms containing H or another substituent as required given the valency of the atom), halogen, cyano, amide, imine, imide, amidine, amine, nitro, hydroxy, ether, carbonyl, carboxy, carbonate, carbamate, phosphine, phosphate, phosphonate, sulphide, sulphone, sulphoxide, alkenyl, alkynyl or silyl.

Ligand Component G

G is a ligand component comprising one or two substituted or unsubstituted carbon atoms and may additionally form part of a fused ring system. Suitable substituents include: alkyl, aryl, alkenyl, heteroaryl, halogen, cyano, amide, imine, imide, amidine, amine, nitro, hydroxy, ether, carbonyl, carboxy, carbonate, carbamate, phosphine, phosphate, phosphonate, sulphide, sulphone, sulphoxide, alkynyl, silyl and substituents containing a functional group that can be polymerised or a polymer chain. Optionally, two substituents may together form a ring or fused ring system. G is covalently connected to two O atoms via a single or double bond.

Examples of ligands L' of formula (5), (6) and (7) include the following:

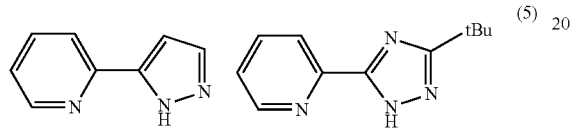
(5)

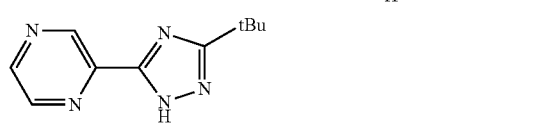

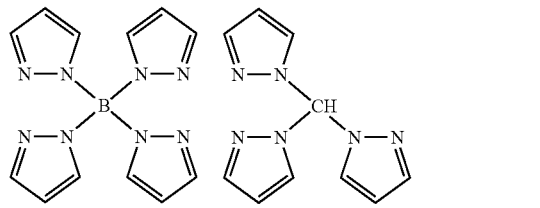

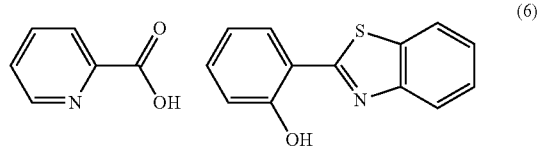
(6)

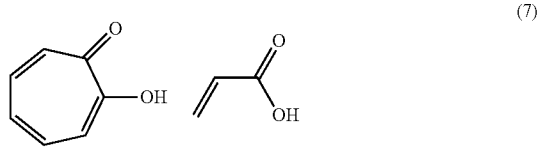
(7)

Complexes:

As described above, the phosphorescent material may be of formula (2):

$$ML_mL'_n \qquad (2)$$

wherein M and L are as defined previously, L' is a bidentate ligand of a different identity to L, m is an integer selected from 1, 2 and 3, and n is an integer selected from 0, 1 and 2. According to one embodiment, m+n=3.

Combining various embodiments described above, the phosphorescent material of one embodiment of the invention is of formula (2):

$$ML_mL'_n \qquad (2)$$

wherein:
M is selected from Ir, Pt, Rh, Pd, Ru and Os,
L is a ligand of formula (1):

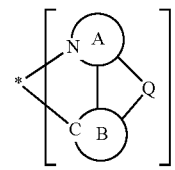
(1)

wherein:
ring A is a 5-membered heterocycle which is unsubstituted or substituted by one or more substituents, containing at least one nitrogen atom as represented in formula (1), which is bound to the metal atom at the asterisk (*),
ring B is a 5- or 6-membered carbocycle or heterocycle which is unsubstituted or substituted by one or more substituents, containing a carbon atom as represented in formula (1) which is bound to the metal atom at the asterisk (*),
rings A and B are joined by a direct covalent bond as represented in formula (1),
rings A and B are joined via a tether Q, wherein
Q is a linear, branched or cyclic alkyl, aryl or alkyl-aryl tether of between 3 and 20 carbon atoms in length, wherein one or more of the carbon atoms in the tether may be replaced with —O—, —S—, —CO—, —CO$_2$—, —CH=CH—, —C≡C—, —NH—, —CONH—, —C=N—, —Si— and —P—, wherein the atoms —Si— and —P— contain substituents based on their valency, and wherein any carbon, nitrogen, silicon or phosphorous atom of the tether may contain one or more substituents selected from the group consisting of halogen, cyano, amide, imine, imide, amidine, amine, nitro, hydroxy, ether, carbonyl, carboxy, carbonate, carbamate, phosphine, phosphate, phosphonate, sulphide, sulphone, sulphoxide, alkenyl, aryl, alkyl, heteroaryl, alkynyl, silyl, and substituents containing a functional group that can be polymerised or a polymer chain, or two substituents may together form a ring or fused ring system, wherein the ring or fused ring system may optionally be attached or fused to one or both of rings A and B,
m is an integer selected from 1, 2 and 3,
L' is a bidentate ligand selected from ligands of formula (5), formula (6) and formula (7):

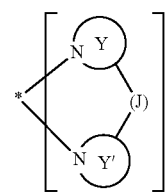
(5)

wherein:
ring Y is a 5-, 6- or 7-membered heterocycle which is unsubstituted or substituted by one or more substituents, containing at least one nitrogen atom as represented in the formula, which is bound to the metal atom at the asterisk (*), ring Y' is a 5-, 6- or 7-membered heterocycle which is unsubstituted or substituted by one or more substituents, and containing at least one nitrogen atom as represented in the formula which is bound to the metal atom at the asterisk (*), and rings Y and Y' are either joined by a direct covalent bond or via a linker J as represented in formula (5), wherein J, when present, is a B, C, O, N, P, Si or S atom which is covalently bonded to both rings Y and Y' and which may be substituted or unsubstituted depending on its valency;

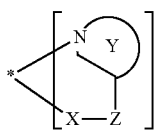
(6)

wherein:
ring Y is as defined previously,
Z is a ligand component connected via a covalent bond to ring Y, and connected to the metal atom via X, and
X is an N, O, S or P atom bound to the metal M at the asterisk (*), wherein the N or P atom is unsubstituted or is substituted;

(7)

wherein
G is a ligand component comprising one or two substituted or unsubstituted carbon atoms, which is connected covalently to two O-atoms; and
the O-atoms are each bound to the metal at the asterisk (*),
n is an integer selected from 0, 1 and 2, and
m+n=2 or 3.

Preparation of the Phosphorescent Materials

The phosphorescent materials of the present invention can be prepared by using synthetic procedures such as those described for example in:

Nonoyama, M., *Bull. Chem. Soc. Jpn.*, 1974, 47, 767

Sergey Lamansky, Peter Djurovich, Drew Murphy, Feras Abdel-Razzaq, Raymond Kwong, Irina Tsyba, Manfred Bortz, Becky Mui, Robert Bau, and Mark E. Thompson *Inorg. Chem.* 2001, 40, 1704-1711

Sergey Lamansky, Peter Djurovich, Drew Murphy, Feras Abdel-Razzaq, Hae-Eun Lee, Chihaya Adachi, Paul E. Burrows, Stephen R. Forrest and Mark E. Thompson *J. Am. Chem. Soc.* 2001, 123, 4304-4312

The phosphorescent materials can be simply prepared by:
reacting a precursor complex of the metal M, with the ligand L, in a ratio suitable to result in a product containing the desired number of ligands L being co-ordinated to the metal M, optionally followed by:
reacting the product with another ligand L' in a ratio suitable to introduce the desired number of ligands L' into the product.

An example of this technique will be described below using Ir as a representative metal. However, it will be appreciated that corresponding phosphorescent materials containing the other metals can be prepared by corresponding techniques.

In one example, a precursor complex of Ir (as the metal), the precursor complex comprising substitutable ligands (in this case, 3 $CH_3COCHCOCH_3$ ligands) is reacted with 3 molar equivalents of ligand L to produce $Ir(L)_3$.

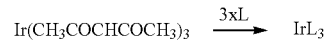

In another example, a precursor complex of Ir comprising substitutable ligands (in this case, the complex is $IrCl_3.3H_2O$, and the ligands are —Cl and $H_2O$) is reacted with 2 molar equivalents of ligand L to produce $[IrL_2Cl]_2$, and this product is reacted with another molar equivalent of ligand L to produce $IrL_3$.

In another example, a precursor complex of Ir comprising substitutable ligands (in this case, the complex is $IrCl_3.3H_2O$, and the ligands are —Cl and $H_2O$) is reacted with 2 molar equivalents of ligand L to produce $[Ir(L)_2Cl]_2$, and this product is reacted with one molar equivalent of ligand L' to produce $IrL_2L'$.

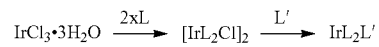

In another example, a precursor complex of Ir in the +1 oxidation state with substitutable ligands (e.g. alkene ligands in a $\eta^2$ hapticity, in this case 1,5-cyclooctadiene) is reacted with 3 molar equivalents of ligand L to produce $IrL_3$ directly.

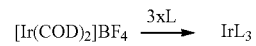

DEFINITIONS OF CHEMICAL TERMS

The term "heterocycle", "heterocyclic" or "heterocyclic group" is well understood in the art of chemistry, and is used to refer to any cyclic groups having between one and five rings, and between 3 to 50 (preferably 5 to 20) ring atoms, of which at least one atom is a heteroatom. In certain embodiments, the heterocyclic group is specifically a 5-membered, 6-membered or 7-membered heterocyclic group (a single-ring heterocyclic group), however the optional substituents for these groups may form a second ring that is fused to the main heterocyclic ring. The heteroatoms may be selected from one or more of O, N, S, Si and P. One subclass of heterocyclic groups are the heteroaromatic (or heteroaryl) groups, which are aromatic groups containing one or more heteroatoms selected from one or more of O, N and S. Such heteroaromatic groups also fall within the definition of aryl group. Some specific examples for heterocyclic groups which may constitute certain moieties in the phosphorescent material are outlined above. Other examples of "heterocyclic groups", "heteroaromatic groups", or "heteroaryl groups" include moieties of imidazole, benzimidazole, pyrrole, furan, thiophene, benzothiophene, oxadiazoline, indoline, carbazole, pyridine, quinoline, isoquinoline, benzoquinone, pyrazoline, imidazolidine, piperidine, etc.

The term "cyclic" is used in its broadest sense to refer to cyclic groups and linked or fused ring systems having between 3 and 50 ring atoms, which may be carbocyclic (containing carbon ring-atoms only) or heterocyclic (containing carbon atoms and at least one heteroatom), and may be saturated or unsaturated. The number of rings is suitably between 1 and 5, preferably 1 or 2. In the case of 5-, 6- and 7-membered cyclic groups, these are single rings containing 5, 6 or 7 ring atoms. In some embodiments, the cyclic group is a carbocycle, that is, a ring containing carbon atoms as the ring atoms. In other instances where the number of ring atoms is not identified, the cyclic group may contain a single ring of any suitable number of ring atoms, or up to 5 linked or fused rings each containing any suitable number of ring atoms.

The term "alkyl" refers to linear or branched alkyl groups or cyclic alkyl groups, comprising between 1 and 20 carbon atoms. These are derived from alkanes. Examples of linear alkyl groups include methyl, propyl or decyl, and examples of branched alkyl groups include iso-butyl, tert-butyl or 3-methyl-hexyl. Examples of cyclic alkyl groups include cyclohexyl and fused alkyl cyclic ring systems.

The term "aryl" or "aryl group" is well understood in the art of chemistry, and is used to refer to any aromatic substituent. The aromatic substituent preferably contains from 1 aromatic ring, up to 4 fused aromatic rings, and between 5 and 50 ring atoms. Aromatic groups are cyclically conjugated molecular entities, containing 4n+2 delocalised π electrons, where n=0 or a positive integer (Hückel 4n+2-rule). Any aromatic groups conforming to this rule are within the definition of aryl. The aryl group may be carbocyclic (i.e. contain carbon and hydrogen only) or may be heteroaromatic (i.e. contain carbon, hydrogen, and at least one heteroatom). The aryl group may be monocyclic such as a phenyl, or a polycyclic aryl group such as naphthyl or anthryl. Examples of aryl groups include a phenyl group, biphenyl group, terphenyl group, naphthyl group, anthryl group, pyrenyl group, etc. The term "aryl" is also used to describe an aromatic ring with any degree of substitution.

The term "alkyl-aryl" refers to a group containing an alkyl group connected to an aryl group.

The term "tether" refers to a chain that joins two groups together, such as the two rings A and B.

The term "halogen" or halo refers to fluorine, chlorine, bromine and iodine.

The term amide refers to substituents containing the group —C(O)NRR', wherein R and R' are selected from H, alkyl, aryl or alkyl-aryl groups, which have been defined previously. The term "imide" refers to substituents containing the group —C(O)NRC(O)R', wherein R and R' are selected from H, alkyl, aryl or alkyl-aryl groups. The term "imine" refers to substituents containing the group —C(=NR)R', wherein R and R' are selected from H, alkyl, aryl or alkyl-aryl groups. The term "amidine" refers to substituents containing the group —C(=NR)NR'R", wherein R, R' and R" are selected from H, alkyl, aryl or alkyl-aryl groups.

The term "amine" refers to the amino group —NH$_2$, and also to secondary and tertiary alkylamino, arylamino and alkylarylamino groups. Examples of an "arylamino group" include a diphenylamino group, ditolylamino group, isopropyldiphenylamino group, t-butyldiphenylamino group, diisopropyldiphenylamino group, di-t-butyldiphenylamino group, dinaphthylamino group, naphthylphenylamino group, etc. Examples of an "alkylamino group" include dimethylamino group, diethylamino group, dihexylamino group, etc.

"Nitro" refers to —NO$_2$. "Cyano" refers to —C≡N. "Hydroxy" refers to —OH.

"Ether" refers to groups containing an ether group R—O—R', wherein R and R' are selected from H, alkyl, aryl or alkyl-aryl groups, which have been defined previously.

"Carbonyl" refers to substituents containing a carbonyl group —C=O. Such groups include ketones (—COR), aldehydes (—CHO), carboxylic acids (—CO$_2$H), enones (—C=O—CR=CR'R"), esters (—CO$_2$R), acyl halides (—COhalogen), acid anhydrides (—C(=O)—O—C(=O)—R') and carbonates R—O—C(=O)—O—R' as examples, where each of R, R' and R" is an alkyl or aryl group. "Carboxyl" refers to substituents containing a carboxylate group (RCO$_2^-$), where R is alkyl or aryl, as examples. "Carbamate" refers to substituents containing a carbamate group —O—C(=O)—NRR', where R and R are typically alkyl or aryl, or may together form a ring.

"Phosphine" refers to —PR$_2$, wherein R is selected from H, alkyl, aryl or alkyl-aryl. "Phosphate" refers to substituents containing the PO$_4$ group, with any suitable end groups such as H, aryl and/or alkyl. Examples include —OP(=O)—(OR)$_2$, where each R is independently H, alkyl, aryl, etc. "Phosphonate" refers to a moiety derived from the removal of an atom from a phosphonate of the formula O=P(OR)$_2$R'.

"Sulphide" refers to —SR where R is H, alkyl or aryl, as an example. "Sulphone" refers to groups containing the unit —S(=O)$_2$—, such as —S(=O)$_2$—R where R is alkyl or aryl, as examples. "Sulphoxide" refers to groups containing the unit —S(=O)—, such as —S(=O)—R where R is alkyl or aryl, as examples.

"Alkenyl" refers to hydrocarbon chains of between 2 and 20 carbon atoms in length containing at least one —C=C— group. Examples include vinyl, allyl (including substituted variants thereof) and all isomers of propenyl, butenyl, heptenyl, hexenyl, etc. "Alkynyl" refers to hydrocarbon chains of between 2 and 20 carbon atoms in length containing at least one —C≡C— group. Examples include propynyl, butynyl, heptynyl, hexynyl, etc.

"Silyl" refers to a moiety of the formula —SiR$_3$ (wherein R is any substituent, such as H, alkyl, aryl, etc), and silyl ethers —SiR'$_2$OR" where R' and R" are any suitable substituents such as alkyl, aryl, and alkyl-aryl, etc. Further examples include a trimethylsilyl group, triethylsilyl group, t-butyldimethylsilyl group, vinyldimethylsilyl group, propyldimethylsilyl group, methyldiphenylsilyl group, dimethylphenylsilyl group, triphenylsilyl group, etc.

According to some embodiments, the ligand may contain a substituent which contains a functional group that can be polymerised or a polymer chain. The functional group or polymer chain may be attached via any suitable divalent linking group, which may be referred to as —R$_{linker}$-. Examples of divalent linking groups include —O—, —NH—, —Nalkyl-, —Naryl-, -alkyl- (such as —(CH$_2$)$_x$—), —CO$_2$—, —CO—, -aryl-, -heteroaryl-, and combinations thereof. Combinations include, as examples, —O-aryl-, —NH-aryl-, —Nalkyl-aryl-, —(CH$_2$)$_x$-aryl-.

Functional groups that can be polymerised include —R$_{linker}$-'CR$_1$=CHR$_2$, where R$_{linker}$ is as defined above, R$_1$ is hydrogen, alkyl, aryl or heteroaryl, and R$_2$ is hydrogen, a halogen atom, nitro group, acetyl group, acrylate group, amide group, cyano group, carboxylate group, sulphonate group, an aryl, an alkyl or a heterocyclic group. Each of these substituents may be further substituted by one or more further substituents selected from the range of possible substituents for A rings identified previously. The point of attachment of the monomer segment is via the carbon atom marked 'C. The monomer may be polymerised subsequently to form a polymeric version of the phosphorescent material. Other examples of functional groups that can be polymerised include amino acids, lactams, hydroxy acids, lactones, aryl halides, boronic acids, alkynes, epoxides and phosphodiesters.

When a pair of substituents together form a ring or fused ring system, the ring may be a single ring of between 5 and 20 atoms in size, in which the ring is carbocyclic or heterocyclic (i.e. the atoms are selected from carbon and heteroatoms), or a fused ring system of between 5 and 50 atoms in size, and containing from 2 to 4 rings. The fused ring system may also be fused to other rings of the subject compound—such as the A or B ring in the case of ligands L of formula (1). Examples of suitable rings and fused rings include those described above in the context of cyclic.

Properties of the Phosphorescent Material

Through selection of the appropriate combination of ring atoms for rings A and B, as well as substituents on these rings, the ancillary ligand(s) L', and the length and identity of the tether Q, it is possible to control the colour of the phosphorescent light emission from the material. Thus, the phosphorescent materials of the present invention can be used to fabricate organic electroluminescent devices which can be tuned to produce an emission colour from 400-800 nm.

Organic Electroluminescent Devices

The invention provides an organic electroluminescent device comprising:
  a pair of electrodes comprising an anode and a cathode, and
  one or more layers of organic compound arranged between the pair of electrodes,
  wherein the organic compound layer, or one or more of the organic compound layers, comprises a phosphorescent material as described above.

The organic electroluminescent device according to the present invention is composed of organic compounds layer(s) aligned between an anode and a cathode.

The organic layer(s) may be constituted by:
  a single layer doped with a phosphorescent material of the present application, or
  multiple layers of which at least one layer may be doped with a phosphorescent material of the present application, or
  multiple layers of which at least one layer may be comprised entirely of a phosphorescent material of the present application.

In the organic electroluminescence device of the present application, the organic compound layer comprising the above-mentioned phosphorescent material of the present application may be formed separately, or together, with the other layers (if any other layers are present) between the pair of electrodes (cathode and anode). Suitable formation techniques include vacuum deposition or solution process.

The thickness of the organic compound layer may be preferably less than at most 10 μm, more preferably less than 0.5 μm, even more preferably 0.001-0.5 μm.

Specific embodiments of the invention will now be described in further detail with reference to the accompanying figures, which illustrate a range of possible arrangements for the device of the present invention. It will be understood that these embodiments are provided by way of example only, and are not intended to limit the scope of the invention.

Figure 2:
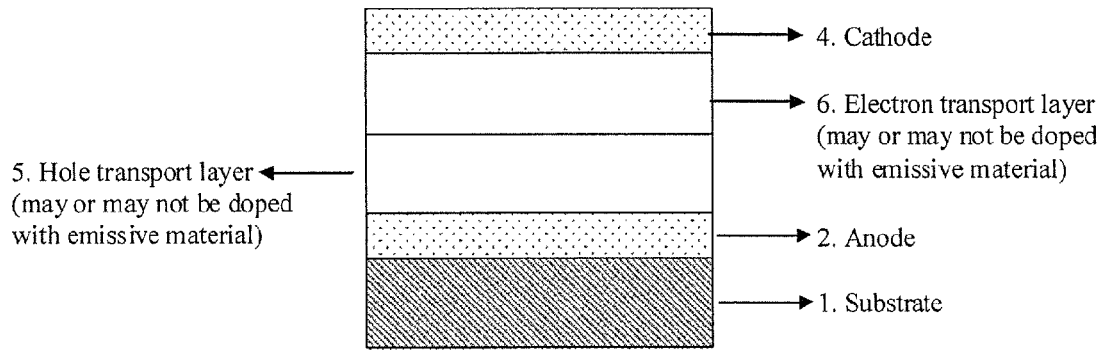
FIG. 2 is a schematic illustration of the basic structure of an organic electroluminescent device according to a second embodiment of the invention.
Figure 3:
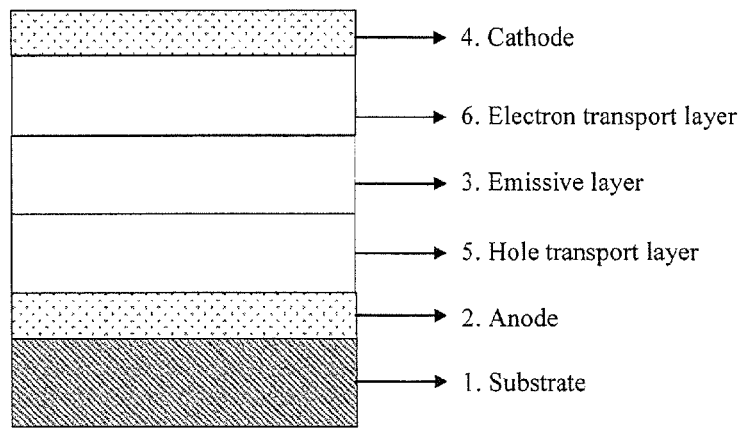
FIG. 3 is a schematic illustration of the basic structure of an organic electroluminescent device according to a third embodiment of the invention.
Figure 4:
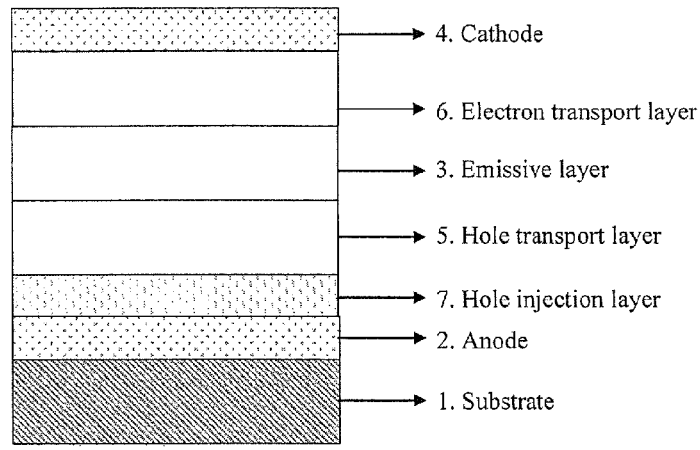
FIG. 4 is a schematic illustration of the basic structure of an organic electroluminescent device according to a fourth embodiment of the invention.

The organic electroluminescent device of embodiments of the present application may have a single layer structure comprised only of the compound as defined by formula (1) as shown in FIG. 1 or be a multiple layered structure of two or more layers as shown in FIGS. 2, 3 and 4.

More specifically, FIG. 1 is a schematic cross section of a first embodiment of the organic electroluminescent device of the present invention. In FIG. 1, the organic electroluminescent device includes a substrate 1, an anode 2 (deposited on the substrate 1), an emission layer 3 (deposited on the anode 2) and a cathode 4 (deposited on the emission layer 3). In this embodiment, the emission layer 3 forms a single organic compound type-layer. This single layer may be composed entirely of a compound having hole transporting ability, electron transporting ability and luminescence ability (associated with the re-combination of electrons and holes) based on its own properties, or through combination of the properties of that material with a host or dopant. According to some embodiments, the phosphorescent material of the present application can serve as a dopant. According to other embodiments, the phosphorescent material of the present application can function as a hole or electron transporting layer.

In FIG. 1, the emission layer 3 may preferably have a thickness of 5 nm to 1 μm, more preferably 5 to 50 nm.

FIG. 2 shows another embodiment of the organic electroluminescent device of the present invention in the form of a multiple layer-type device including a hole transporting layer 5 and an electron transporting layer 6.

Referring to FIG. 2, the organic electroluminescent device includes a substrate 1 and an anode 2 (deposited on the substrate 1). The hole transporting layer 5 is deposited on the anode 2. The electron transporting layer 6 is deposited on the hole transporting layer 5, and a cathode 4 is deposited on the electron transporting layer 6. In this embodiment, the hole transporting layer 5 and the electron transporting layer 6 may contain the phosphorescent material of the present application as a dopant(s) for forming a emission layer 3.

In the embodiment of FIG. 2, each of the hole transporting layer 5 and the electron transporting layer 6 may have the thickness of 5 nm to 1 μm, more preferably 5 nm to 50 nm.

FIG. 3 shows another embodiment of the organic electroluminescent device of the present invention in the form of a multiple layer-type device comprising a hole transporting layer 5, an emission layer 3 and an electron transporting layer 6. In FIG. 3, the organic electroluminescent device includes a substrate 1, an anode 2 (deposited on the substrate 1), a hole transporting layer 5 (deposited on the anode 2), an emission layer 3 (deposited on the hole transporting layer 5), an electron transporting layer 6 (deposited on the emission layer 3) and a cathode 4 (deposited on the electron transporting layer 6). In this embodiment, each of the hole transporting layer 5, the emission layer 3 and the electron transporting layer 6 may be formed by use of a hole transporting compound, an emissive compound and an electron transporting compound, respectively or as a mixture of these kinds of compounds. The phosphorescent material of the present application can form the emission layer 3, or be a component (such as a dopant) of the hole transporting layer 5, or be a component (such as a dopant) of the electron transporting layer 6.

FIG. 4 shows another embodiment of the organic electroluminescent device of the present invention with multiple layers comprising a hole injection layer 7, a hole transporting layer 5, an emission layer 3 and an electron transporting layer 6. In FIG. 4, the organic electroluminescent device includes a substrate 1, an anode 2 (deposited on the substrate 1), a hole injection layer 7 (deposited on the anode 2), a hole transporting layer 5 (deposited on the hole injection layer 7), an emission layer 3 (deposited on the hole transporting layer 5), an electron transporting layer 6 (deposited on the emission layer 3) and a cathode 4 (deposited on the electron transporting layer 6). In this embodiment, each of the hole injection layer 7, the hole transporting layer 5, the emission layer 3 and the electron transporting layer 6 may be formed by use of a hole injection compound, a hole transporting compound, an emissive compound and an electron transporting compound, respectively, or as a mixture of these kinds of compounds. The phosphorescent material of the present application can form the emission layer, or be a component (such as a dopant) in the hole transporting layer 5 or the electron transporting layer 6.

In FIGS. 1, 2, 3 and 4, each layer may be formed by either vacuum deposition or wet process using low molecular weight or polymer compounds or a mixture of low molecular weight and polymer compounds. Each thickness of the layer 3, 5 and 6 may preferably range from 1 nm to 1 µm. Each of the thickness of the cathode and the anode may be preferably 100-200 nm The organic layer structures in the devices shown in FIGS. 1, 2, 3 and 4 represent the basic structure, respectively, so that the structure may be appropriately optimized depending on characteristics demanded. Examples of suitable modifications include the incorporation of one or more additional layers.

For example, the hole transporting layer may be altered to comprise a hole injection layer (deposited on the anode) and hole transporting layer (deposited on the hole injection layer).

More specific embodiments of the device structure other than those of FIGS. 1, 2, 3 and 4 are shown below, but not restricted to these device structures.
(1) Anode/hole transporting layer/emission layer/electron transporting layer/electron injection layer/cathode
(2) Anode/hole injection layer/emission layer/electron transporting layer/electron injection layer/cathode
(3) Anode/charge blocking layer/hole transporting layer/ emission layer/electron transporting layer/cathode
(4) Anode/hole transporting layer/emission layer/electron transporting layer/charge blocking layer/cathode
(5) Anode/inorganic semiconductor/charge blocking layer/ hole transporting layer/emission layer/charge blocking layer/cathode
(6) Anode/charge blocking layer/hole transporting layer/ emission layer/electron transporting layer/charge blocking layer/cathode
(7) Anode/charge blocking layer/hole injection layer/hole transporting layer/emission layer/electron transporting layer/electron injection layer/cathode
(8) Anode/charge blocking layer/hole injection layer/hole transporting layer/emission layer/electron transporting layer/electron injection layer/charge blocking layer/cathode In the embodiments described above, more preferable device structures are (1), (2), (3), (7) and (8), although this is not a restriction. According to some embodiments, the phosphorescent material of the present application may be formed as an emission layer, or as a dopant in a hole transport layer or an electron transport layer. According to some embodiments, there is provided the use of the phosphorescent material of the present application as an emission material in an organic electroluminescence device, or as a dopant in a hole transport layer, or as a dopant in an electron transporting layer.

In some embodiments, the phosphorescent material of the present application may be used in combination with one or more of a hole injection material, a hole transporting compound (or material), an electron transporting compound and/or an additional emission compound, examples of which may include the following:

Exemplary hole transporting materials/compounds include:

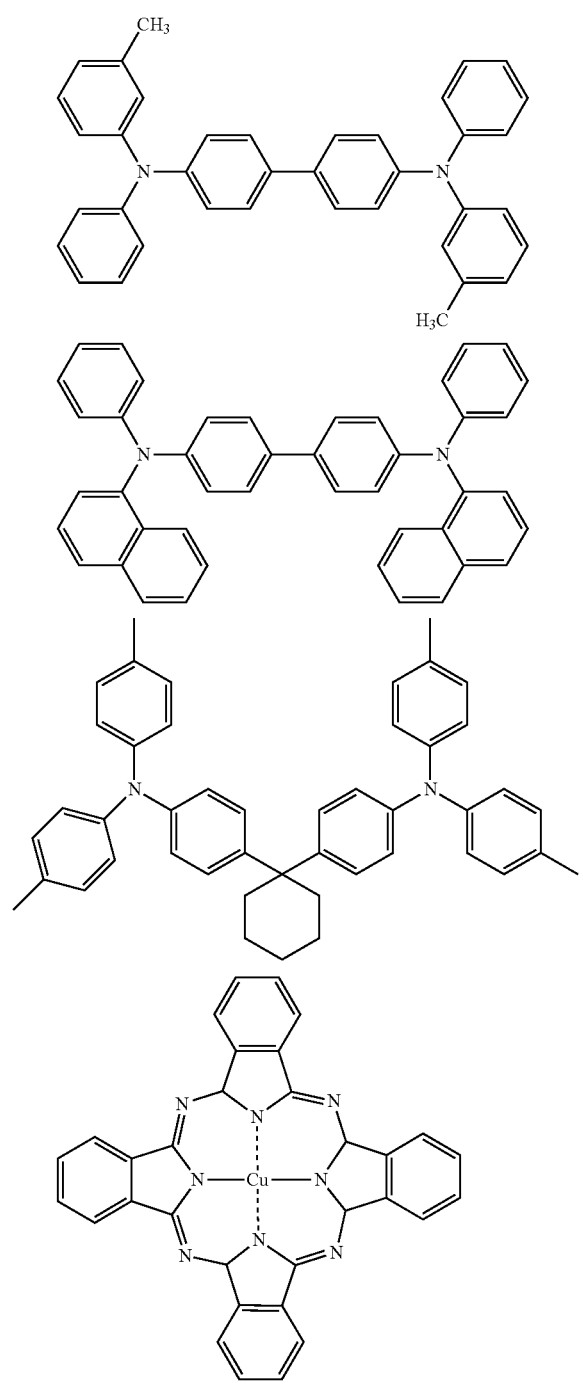

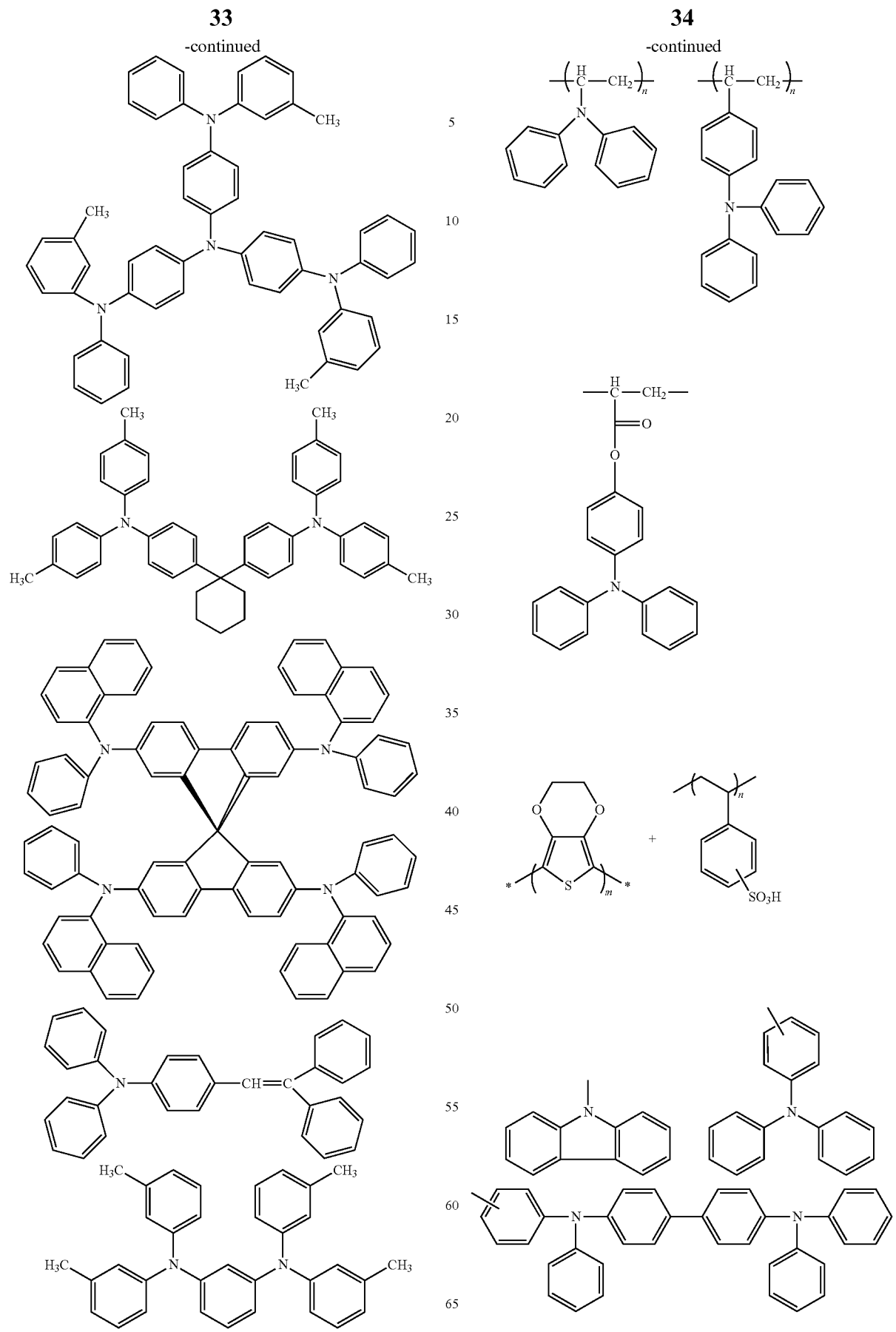

Exemplary electron transporting materials/compounds include:
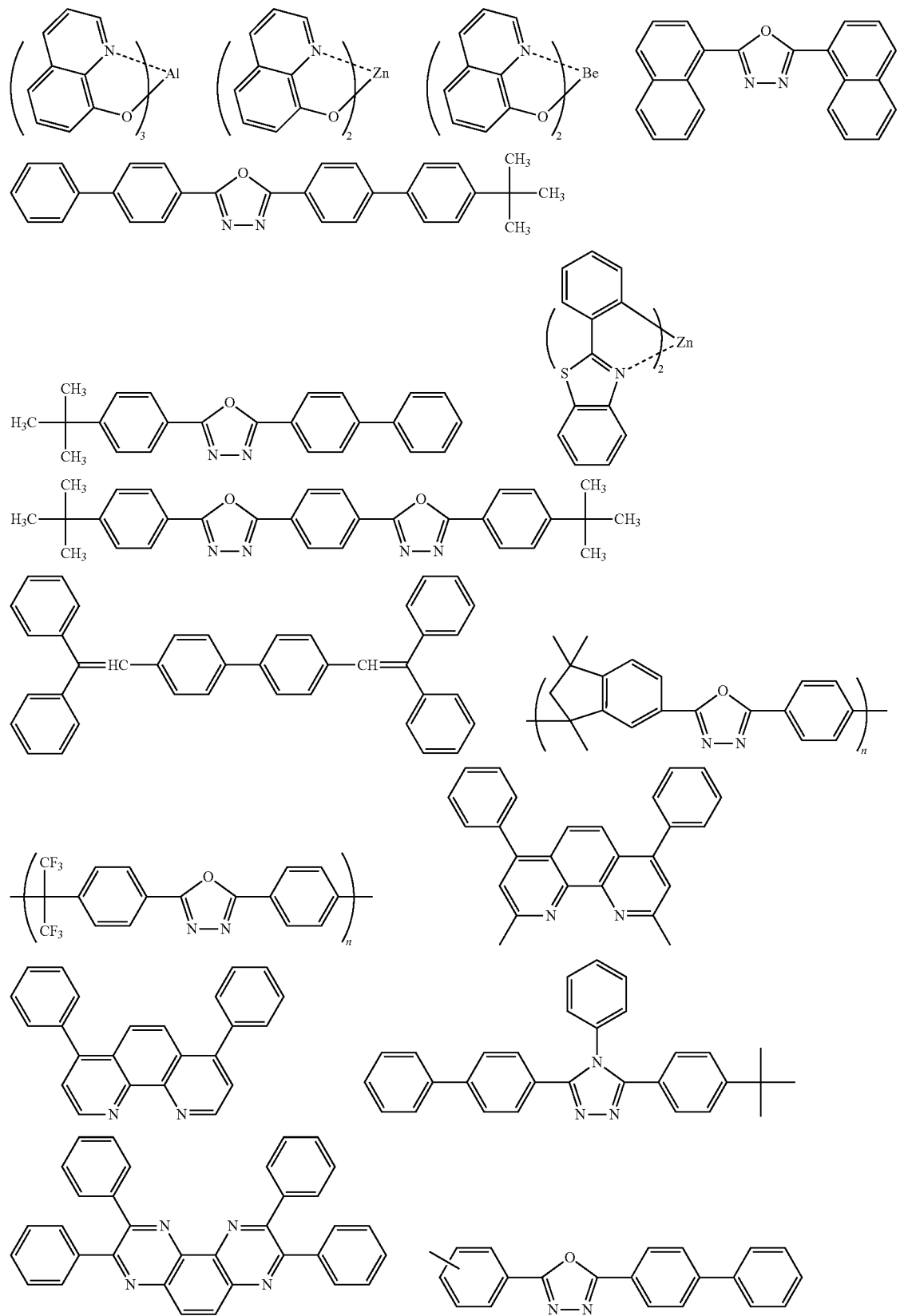

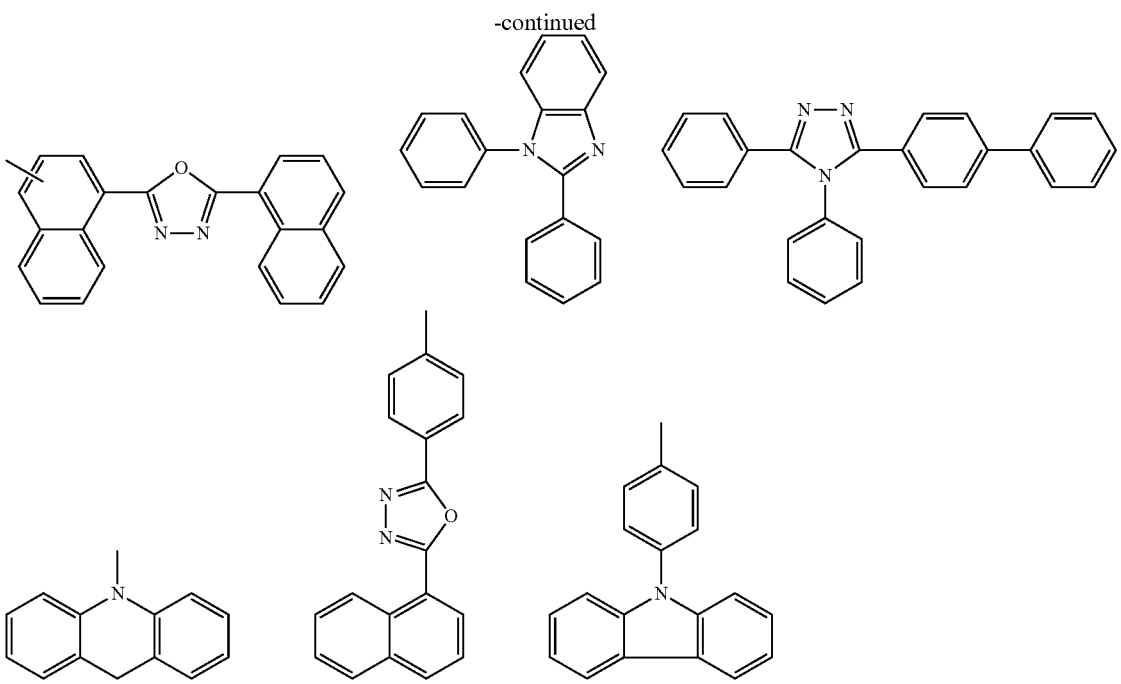

As a material for the anode (e.g. 2 in the Figures), it is preferred to use one having a large work function, examples of which may include metals, such as gold, platinum, nickel, palladium, cobalt, selenium, vanadium and their alloys; metal oxides, such as tin oxide, zinc oxide, indium zinc oxide (IZO) and indium tin oxide (ITO) and electroconductive polymers, such as PEDOT:PSS, polyaniline, polypyrrole and polythiophene and derivatives thereof. These compounds may be used singly or in combination of two or more species.

As a material for the cathode (e.g. 4 in the Figures), it is preferred to use one having a smaller work function, usually under 4.0 eV, examples of which may include; metals such as sodium, magnesium, calcium, lithium, potassium, aluminium, indium, silver, lead, chromium and their alloys, or oxides.

The charge blocking layer may be deposited adjacent to either electrode to avoid current leakage as mentioned in embodiments (3) to (8). As the charge blocking material, it is preferred to use an inorganic compound, examples of which may include aluminium oxide, lithium fluoride, lithium oxide, caesium oxide, magnesium oxide, magnesium fluoride, calcium oxide, calcium fluoride, aluminium nitride, titanium oxide, silicon oxide, silicon nitride, boron nitride, vanadium oxide.

The substrate (e.g., 1 shown in the Figures) for the organic electroluminescence device of the present invention may include an opaque substrate made from any suitable material, such as metal or ceramics, or a transparent substrate made from any suitable transparent material such as glass, quartz, plastics, etc.

The devices of the present application can be provided in the form of a stacked organic electroluminescent (EL) device. The present application also extends to electronic devices comprising the organic electroluminescent device of the present invention, including displays and light sources.

EXAMPLES

The present invention will be described below in detail with preparation examples and the device examples, but the present invention is not intended to be restricted to these examples.

Example 1

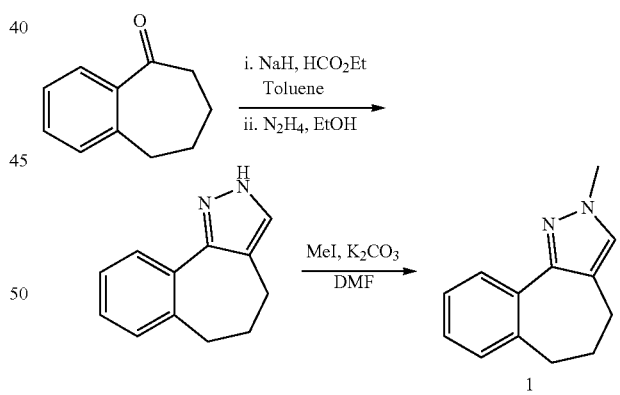

To a suspension of NaH (80%, 1.9 g, 62.8 mmol) in toluene (100 ml) was added a solution of 6,7,8,9-tetrahydro-5H-benzo[7]annulen-5-one (5 g, 31.2 mmol) and ethyl formate (5 mL, 61.4 mmol) in toluene (50 mL) dropwise at 0° C. Upon complete addition, methanol (0.01 mL) was added and the reaction was warmed to room temperature. After 2 h the reaction was quenched by the addition of aqueous $NH_4Cl$ (20 mL) and extracted into EtOAc (100 mL), dried over $MgSO_4$ and the solvent was evaporated. The crude product was dissolved in EtOH (50 mL) and hydrazine hydrate (2.3 mL, 36.8 mmol) was added. The reaction mixture was heated at an oil bath temperature of 95° C. After 1.5 hours the reaction was worked up. The solution was cooled to room temperature and solvent was evaporated under reduced pressure. Precipitation from heptane gave the crude N—H pyrazole which was used without further purification. $^1$H NMR (200 MHz, CDCl$_3$) 7.78-7.74 (1H, m, ArH), 7.47 (1H, s, pzH), 7.26-7.20 (3H, m, ArH), 2.86-2.80 (4H, m, CH$_2$CH$_2$), 2.12-2.00 (2H, m, CH$_2$). The crude pyrazole (4 g, 21.7 mmol) and K$_2$CO$_3$ (3 g, 21.7 mmol) were taken up in DMF (10 mL). Iodomethane (1.4 mL, 21.7 mmol) was then added and the reaction mixture was allowed to stir at an oil bath temperature of 80° C. for 1 hour. The reaction was then allowed to cool to room temperature and diluted with water (100 mL) and extracted with EtOAc (50 mL). The organic phase was washed twice more with water (2×100 mL). The combined organic phases were dried over MgSO$_4$ and the solvent was evaporated to give a mixture of N-methylated pyrazoles in a 6:1 ratio by $^1$H NMR. Purification by chromatography on silica (CH$_2$Cl$_2$ as eluant) gave 2.8 g (65% yield) of the desired N-methylpyrazole 1 (first eluting isomer, confirmed by NOESY). $^1$H NMR (400 MHz, CDCl$_3$) 7.97-7.93 (1H, m, ArH), 7.27-7.16 (4H, m, 3×ArH and pzH). 3.92 (3H, s, NCH), 2.83-2.70 (4H, m, CH$_2$CH$_2$), 2.13-2.00 (2H, m, CH$_2$). The product was confirmed by GC-MS, m/z=198.

Example 2

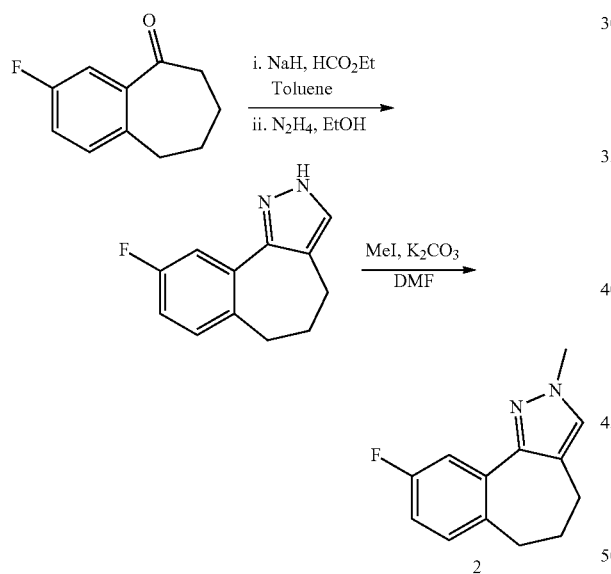

A solution of 2-fluoro-6,7,8,9-tetrahydro-5H-benzo[7]annulen-5-one (2 mL, 13 mmol) and ethyl formate (1.6 mL, 19.5 mmol) in toluene (50 mL) was added dropwise to a suspension of NaH (0.58 g, 19.5 mmol) in toluene (100 mL) at 0° C. Upon complete addition methanol (0.05 ml, 1.302 mmol) was added and the reaction allowed to stir at room temperature. Gas evolution was observed. The reaction was monitored by $^1$H NMR after 1.5 hours and showed ca. 50% conversion. A further 1 equivalent of NaH (0.58 g) and 1.5 equivalents of EtOCHO (1.5 mL) was then added and the reaction was allowed to stir at room temperature over night. The reaction was deemed complete by $^1$H NMR analysis. The reaction was quenched by the addition of aqueous NH$_4$Cl (50 mL), and extracted into EtOAc (100 mL). The organic phase was washed with water (100 mL) and brine (100 mL), dried over anhydrous MgSO$_4$ and the solvent was evaporated. The crude reaction product was then taken up in EtOH (50 mL) and hydrazine hydrate (0.98 ml, 19.5 mmol) was added. The reaction was heated at oil bath temperature of 90° C. for 1 hour and then cooled to room temperature and the solvent was concentrated. The crude product precipitated and was washed with heptane and isolated as yellow solid (2.2 g, 84% yield). $^1$H NMR (200 MHz, CDCl$_3$) 7.50-7.44 (2H, m, ArH and pzH), 7.18-7.10 (1H, m, ArH), 6.94-6.85 (1H, m, ArH), 2.86-2.77 (4H, m, CH$_2$CH$_2$), 2.10-2.97 (2H, m, CH$_2$). The crude pyrazole (5 g, 24.7 mmol) was taken up in DMF (25 mL) and iodomethane (2.3 ml, 37.1 mmol) and K$_2$CO$_3$ (5.1 g, 37.1 mmol) were added. The reaction mixture was heated at an oil bath temperature of 100° C. for 1 hour. The reaction was then cooled to room temperature, diluted with water (100 mL) and extracted with EtOAc (50 mL). The organic phase was then washed twice with water (2×100 mL), dried over MgSO$_4$ and the solvent was evaporated. The crude product was obtained as a 6:1 mixture of regioisomers (by $^1$H NMR). Purification was carried out by chromatography on silica (CH$_2$Cl$_2$ to 2% MeOH in CH$_2$Cl$_2$ as eluant). The desired N-methylpyrazole 2 was isolated as the first eluting isomer (3.2 g, 60% yield) and confirmed by NOESY. $^1$H NMR (400 MHz, CDCl$_3$) 7.70-7.67 (1H, m, ArH), 7.20 (1H, s, pzH), 7.11-7.07 (1H, m, ArH), 6.88-6.83 (1H, m, ArH), 3.91 (3H, s, NCH$_3$), 2.79-2.73 (4H, m, CH$_2$CH$_2$), 2.02-1.99 (2H, m, CH$_2$).

Example 3

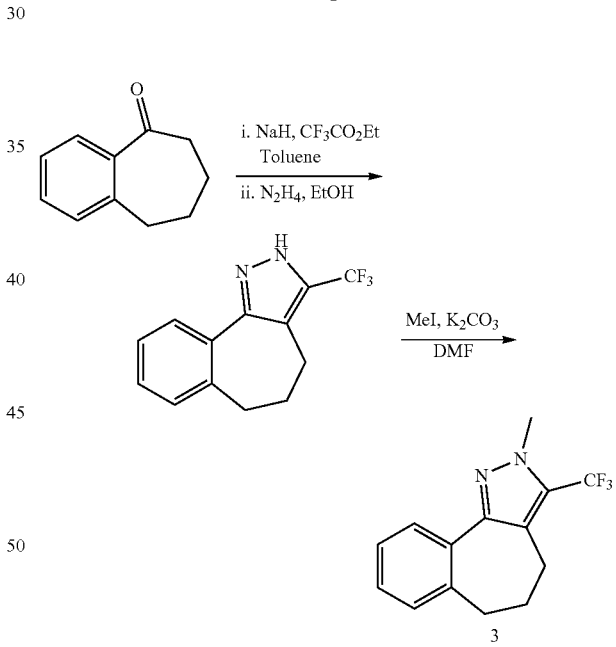

Sodium hydride (2.00 g, 66.8 mmol) was suspended in THF (100 mL) and 6,7,8,9-tetrahydro-5H-benzo[7]annulen-5-one (5 mL, 33.4 mmol) was added dropwise. The reaction was heated at reflux for 2 hours. The reaction mixture was then allowed to cool to room temperature and ethyl trifluoroacetate (5.9 ml, 50 mmol) was added via a syringe. Stirring was continued at room temperature for 2 hours. The reaction was worked up by quenching with 0.5M KHSO$_4$ (100 mL) and extracted with EtOAc (100 mL). The organic phase was washed with water (100 mL) and dried over MgSO$_4$. The solvent was evaporated to give the crude N—H-pyrazole which was used without further purification.

The N—H-pyrazole was taken up in EtOH and hydrazine hydrate (2.5 mL, 50.1 mmol) was added. The reaction was allowed to stir at an oil bath temperature of 80° C. for 1 hour and then cooled to room temperature and the solvent was evaporated. The crude pyrazole was isolated and used without further purification. $^1$H NMR (400 MHz, CDCl$_3$), 7.53-7.51 (1H, m, ArH), 7.33-7.21 (3H, m, ArH), 2.93 (2H, m, CH$_2$), 2.82 (2H, m, CH$_2$), 2.07-2.10 (2H, m, H$_2$). The crude pyrazole (3.9 g, 15.4 mmol), K$_2$CO$_3$ (4.3 g, 30.9 mmol) and iodomethane (1.1 mL, 17 mmol) were combined in DMF (30 mL) at room temperature and allowed to stir for 1 hour. The reaction was worked up by diluting with water (100 mL) and extracting into EtOAc. The organic phase was washed a further 2 times with water (100 mL), dried over MgSO$_4$ and the solvent was evaporated under reduced pressure. The crude product was isolated as a 1:1 mixture of regioisomers (by $^1$H NMR) which was purified by chromatography on silica (10% EtOAc in hexane as eluant). 1.8 g (46% yield) of desired N-methylpyrazole 3 was isolated (first eluting isomer, confirmed by NOESY). $^1$H NMR (CDCl$_3$, 400 MHz) 7.90-7.92 (1H, m, ArH), 7.30-7.17 (3H, m, ArH), 4.03 (3H, br s, NCH$_3$), 2.84-2.76 (4H, m, CH$_2$CH$_2$), 2.12-2.06 (2H, m, CH$_2$). $^{19}$F (CDCl$_3$, 188 MHz) −58.4 ppm Example 4

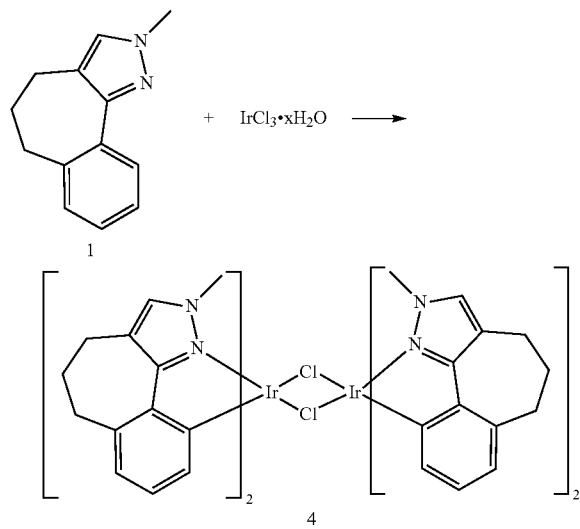

A 250 ml one necked flask was charged with 1.8 g (9.1 mmol) of the pyrazole ligand 1, 1.3 g (3.6 mmol) IrCl$_3$ and 48 ml of a 3:1 mixture of 2-ethoxyethanol and water. The mixture was degassed with N$_2$ for 20 min and heated under an atmosphere of nitrogen at an oil bath temperature of 125° C. for 2.5 hours. After this time the reaction was complete by NMR analysis. The solvent was removed under vacuum and the residue was refluxed in 22 ml acetone to remove the by-product. The product was collected by filtration and dried under vacuum to give 1.95 g (69%) of the desired dimer 4. $^1$H NMR (200 MHz, CD$_2$Cl$_2$), 7.35 (4H, s, pzH), 6.59-6.37 (8H, m, ArH), 5.70-5.59 (4H, m, ArH), 3.80 (12H, s, NCH$_3$), 3.10-2.86 (16H, m, CH$_2$), 2.27-1.75 (8H, m, CH$_2$) ppm. ESI-MS: m/z calc. [C$_{26}$H$_{26}$N$_4$$^{191}$Ir$^{35}$Cl$_2$]$^-$ 655.1. found 655.2; m/z calc. [C$_{26}$H$_{26}$N$_4$$^{191}$Ir]$^+$ 585.2. found 585.2.

Ligand 1 may alternatively be reacted with other metal reagents derived from Pt, Rh, Pd, Ru or Os.

Example 5

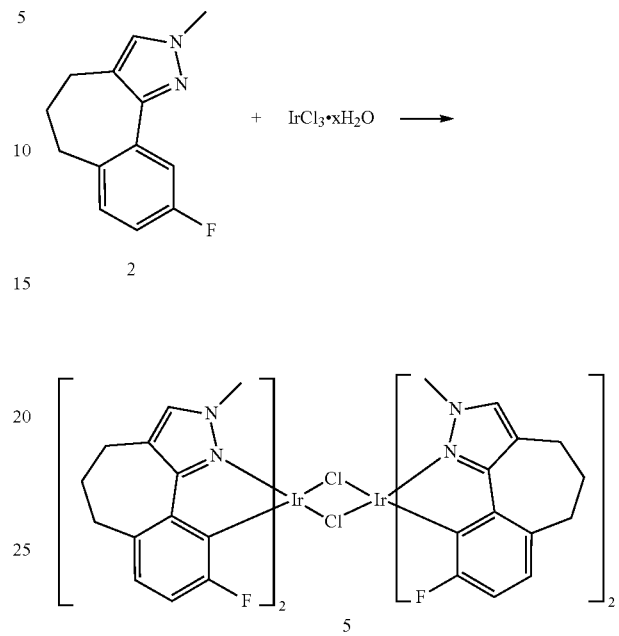

A 50 ml one necked flask was charged with 1.2 g (5.55 mmol) of the fluoro-pyrazole ligand 2, 783 mg (2.22 mmol) IrCl$_3$ and 30 ml of a 3:1 mixture of 2-ethoxyethanol and water. The mixture was degassed with N$_2$ for 20 min and heated under an atmosphere of nitrogen at an oil bath temperature of 125° C. for 1 hour. After this time the reaction was complete by NMR analysis. The solvent was removed under vacuum and the residue refluxed in 20 ml acetone to remove the by-product. The product was collected by filtration and dried in vacuum to give 1.3 g (72%) of the desired dimer 5. $^1$H NMR (200 MHz, CDCl$_3$), 7.20 (4H, s, pzH), 6.50-6.39 (4H, m, ArH), 6.11-5.98 (4H, m, ArH), 3.57 (12H, s, NCH$_3$), 3.05-2.82 (16H, m, CH$_2$), 2.15-2.01 (4H, m, CH$_2$), 1.95-1.72 (4H, m, CH$_2$) ppm. $^{19}$F NMR (188 MHz, CDCl$_3$) −116.10 ppm. ESI-MS: m/z calc. [C$_{26}$H$_{24}$N$_4$F$_2$$^{191}$Ir$^{35}$Cl$_2$]$^-$ 691.1. found 691.0; m/z calc. [C$_{26}$H$_{24}$N$_4$F$_2$$^{191}$Ir]$^+$ 621.2. found 621.2.

Ligand 2 may alternatively be reacted with other metal reagents derived from Pt, Rh, Pd, Ru or Os.

Example 6

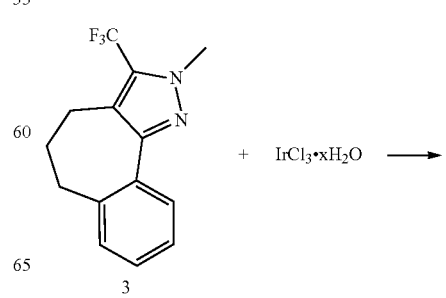

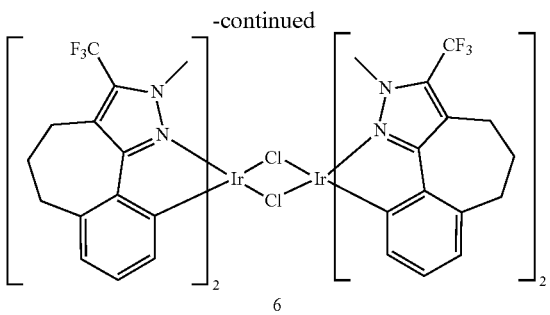

6

The pyrazole 3 (1 g, 3.76 mmol) and iridium(III) chloride (0.571 g, 1.71 mmol) were combined in ethoxyethanol (10 ml)/water (3 ml) and degassed. The reaction mixture was heated under an atmosphere of $N_2$ at an oil bath temperature of 130° C. for 4 hours. The reaction was then allowed to cool to room temperature and concentrated. The crude reaction residue was taken up in $CH_2Cl_2$ and washed with water, saturated aqueous $NaHCO_3$ and brine, dried over $MgSO_4$ and the solvent was evaporated. The crude product was treated with $Et_2O$ and the yellow precipitate was filtered. Dimer 6 (1 g, 77% yield) was used without further purification. $^1$H NMR (200 MHz, $CDCl_3$), 6.53-6.43 (8H, m, ArH), 5.55-5.50 (4H, m, ArH), 4.06 (12H, br s, $NCH_3$), 3.17-2.94 (16H, m, $CH_2CH_2$), 2.26-2.13 (4H, m, CHH), 1.91-1.79 (4H, m, CHH). $^{19}$F ($CDCl_3$, 188 MHz) −57.5 ppm. ESI-MS: m/z calc. $[C_{28}H_{24}N_4F_6{}^{191}Ir^{35}Cl_2]^−$ 791.1. found 791.1; m/z calc. $[C_{28}H_{24}N_4P_6{}^{191}Ir]^+$ 723.2. found 723.2.

Ligand 3 may alternatively be reacted with other metal reagents derived from Pt, Rh, Pd, Ru or Os.

Example 7

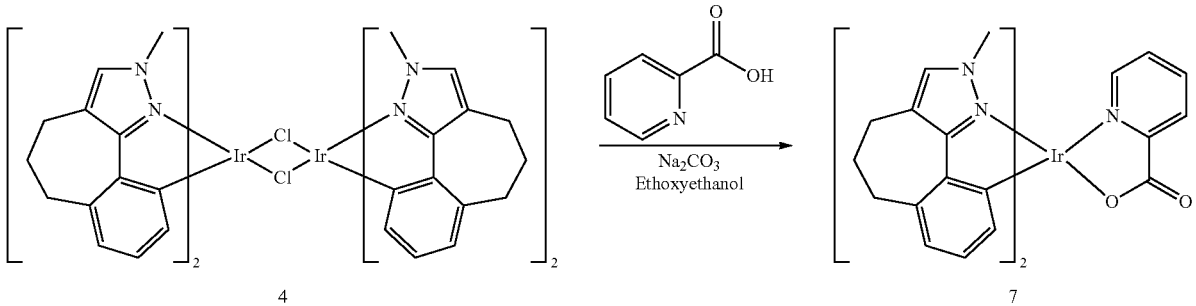

Dimer 4 (100 mg, 0.08 mmol), picolinic acid (25 mg 0.20 mmol) and sodium carbonate (90 mg, 0.85 mmol) were taken up in 4 ml of 2-ethoxyethanol. The mixture was degassed with $N_2$ and heated under an atmosphere of nitrogen at an oil bath temperature of 60° C. for one hour. After this time the reaction was complete as indicated by NMR analysis. The solvent was removed under reduced pressure, $CH_2Cl_2$ was added and the excess $Na_2CO_3$ was filtered off. The remaining solution was reduced to half its volume, the product was precipitated into n-hexane and collected by filtration to give 76 mg (67%) of the desired heteroleptic complex 7.

$^1$H NMR (200 MHz, $CDCl_3$), 8.35-8.25 (1H, m, pyH), 7.89-7.79 (2H, m, pyH), 7.38-7.28 (1H, m, pyH), 7.13 (1H, s, pzH), 7.06 (1H, s, pzH) 6.67-6.48 (4H, m, ArH), 6.17-6.09 (1H, m, ArH), 5.86-5.75 (1H, m, ArH), 3.84 (3H, s, $NCH_3$), 3.02 (3H, s, $NCH_3$) 3.12-2.73 (8H, m, $CH_2$), 2.23-1.84 (4H, m, $CH_2$) ppm. EI-MS: m/z calc. $C_{32}H_{30}{}^{191}IrN_5O_2$ 707.2. found 707.2.

Example 8

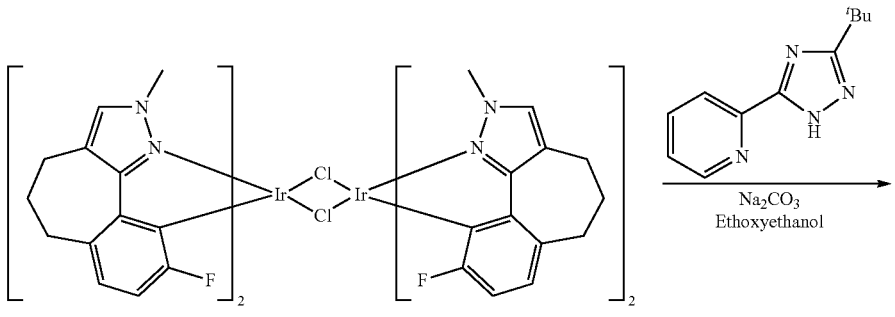

5

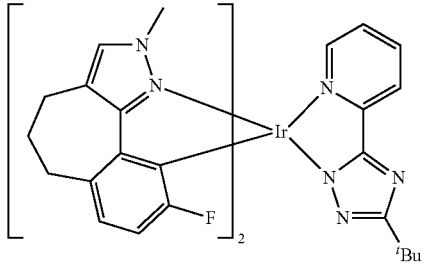

8

Dimer 5 (1.19 g, 0.9 mmol), 2-(3-tert-butyl-1H-1,2,4-triazol-5-yl)pyridine (457 mg 2.26 mmol) and sodium carbonate (958 mg, 9 mmol) were dissolved in 159 ml 2-ethoxyethanol. The mixture was degassed with $N_2$ and heated under an atmosphere of nitrogen at an oil bath temperature of 90° C. for ninety minutes. After this time the reaction was complete as indicated by NMR analysis. The solvent was removed under reduced pressure, $CH_2Cl_2$ was added and the excess $Na_2CO_3$ was filtered off. The solvent was removed and the residue was purified by chromatography on silica (EtOAc:hexane mixtures as eluent) to give 1.29 g of the desired product 8 (86% yield). $^1$H NMR (200 MHz, $CDCl_3$) 8.21-8.10 (1H, m, ArH), 7.84-7.66 (2H, m, ArH), 7.06-6.96 (1H, m, ArH), 6.93-6.87 (2H, m, ArH), 6.75-6.58 (2H, m, ArH), 6.40-6.22 (2H, m, ArH), 3.12-2.99 (4H, m, $CH_2$), 2.96 (3H, s, $NCH_3$), 2.94 (3H, s, $NCH_3$), 2.88-2.62 (4H, m, $CH_2$), 2.17-1.96 (4H, m, $CH_2$), 1.32 (9H, s, $C(CH_3)_3$ ppm. $^{19}$F NMR ($CDCl_3$, 188 MHz) −112.6, −114.9 ppm EI-MS: m/z calc. $C_{37}H_{37}F_2^{191}IrN_8$ 822.3. found 822.4.

Example 9

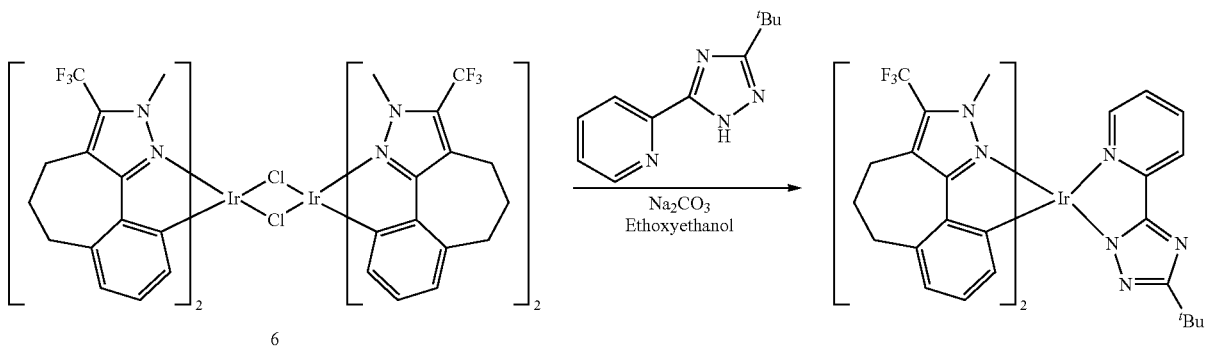

Dimer 6 (50 mg, 0.033 mmol), 2-(3-tert-butyl-1H-1,2,4-triazol-5-yl)pyridine (17 mg. 0.082 mmol) and sodium carbonate (8.74 mg, 0.082 mmol) were taken up in 2-ethoxyethanol (10 mL) and heated under an atmosphere of nitrogen at an oil bath temperature of 80° C. for 90 minutes. The reaction mixture was allowed to cool to room temperature and the solvent was evaporated. The residue was diluted in $CH_2Cl_2$ and filtered through a pad of celite. Purification of the crude product was carried out by chromatography on silica (4:1 EtOAc/Hexane as eluant) to give 50 mg of the desired product 9 (82% yield). $^1$H NMR (200 MHz, $CDCl_3$) 8.21-8.16 (1H, m, ArH), 7.74-7.73 (1H, m, ArH), 7.63-7.61 (1H, m, ArH), 7.06-6.99 (1H, m, ArH), 6.73-6.67 (4H, m, ArH), 6.13-6.09 (1H, m, ArH), 5.97-5.89 (1H, m, ArH), 3.24 (3H, s, $NCH_3$), 3.15 (3H, s, $NCH_3$), 3.08-2.98 (8H, m, $CH_2$), 2.21-1.99 (4H, m, $CH_2$) 1.32 (9H, s, $C(CH_3)_3$. EI-MS: m/z calc. $C_{39}H_{37}F_6^{191}IrN_8$ 922.3. found 922.3. Structure confirmed by x-ray crystallography.

Example 10

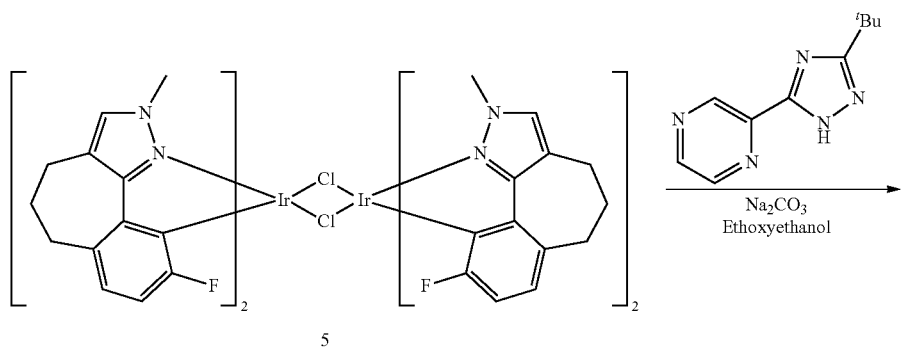

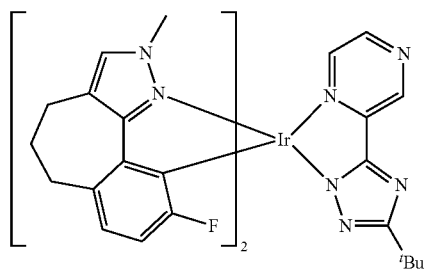

Dimer 5 (150 mg, 0.11 mmol), 2-(3-tert-butyl-1H-1,2,4-triazol-5-yl)pyrazine (69 mg. 0.34 mmol) and sodium carbonate (121 mg, 1.14 mmol) were dissolved in 20 ml 2-ethoxyethanol. The mixture was degassed with $N_2$ and heated under an atmosphere of nitrogen at an oil bath temperature of 80° C. for ninety minutes. After this time the reaction was complete as indicated by NMR analysis. The solvent was removed under reduced pressure, $CH_2Cl_2$ was added and the excess $Na_2CO_3$ was filtered off. The solvent was removed and the residue was purified by chromatography on silica (EtOAc as eluent) to give 144 mg of the desired product 10 (77% yield). $^1$H NMR (200 MHz, CDCl$_3$) 9.38 (1H, d, J=1.4 Hz, pyzH), 8.25 (1H, d, J=3.1 Hz, pyzH), 7.74 (1H, dd, J=3.1, 1.4 Hz, pyzH), 6.93 (1H, s, pzH), 6.91 (1H, s, pzH), 6.77-6.57 (2H, m, ArH), 6.45-6.21 (2H, m, ArH), 3.11-2.98 (4H, m, CH$_2$) 2.96 (3H, s, NCH$_3$), 2.92 (3H, s, NCH$_3$), 2.89-2.59 (4H, m, CH$_2$), 2.18-1.91 (4H, m, CH$_2$), 1.33 (9H, s, C(CH$_3$)$_3$) ppm. $^{19}$F NMR (CDCl$_3$, 188 MHz) −112.4, −115.3 ppm ESI-MS: m/z calc. [C$_{36}$H$_{36}$F$_2$$^{191}$IrN$_9$+1]$^−$ 824.2. found 824.2. Emission λ at 295.15 K (excitation λ of 340 nm, THF) 572 nm. Q.Y. 0.10 (absolute, THF).

Figure 5:
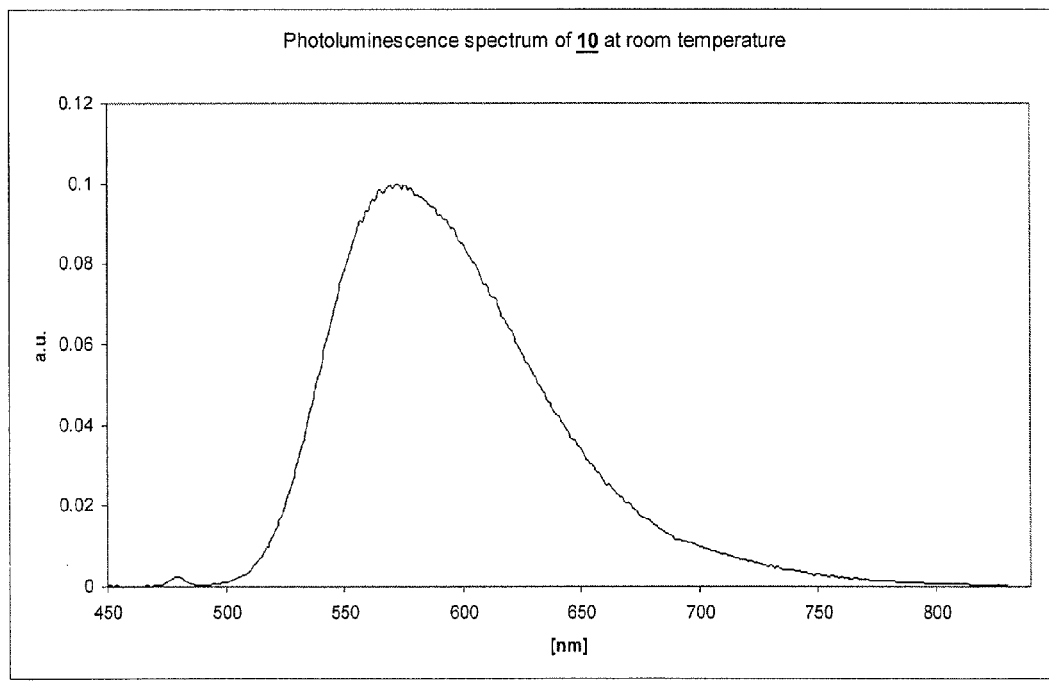
FIG. 5 shows the emission spectrum of the compound exemplified below as 10 at room temperature.

The emission spectrum of this compound is shown in FIG. 5.

Example 11

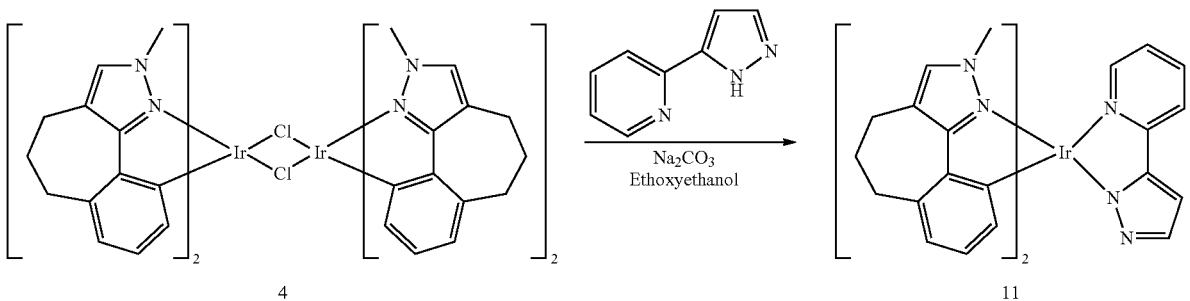

Dimer 4 (150 mg, 0.12 mmol), 2-(1H-pyrazol-5-yl)pyridine (43 mg 0.3 mmol) and sodium carbonate (128 mg, 1.2 mmol) were dissolved in 21 ml 2-ethoxyethanol. The mixture was degassed with $N_2$ and heated under an atmosphere of nitrogen at an oil bath temperature of 80° C. for ninety minutes. After this time the reaction was complete as indicated by NMR analysis. The solvent was removed under reduced pressure, $CH_2Cl_2$ was added and the excess $Na_2CO_3$ was filtered off. The solvent was removed and the residue was purified by chromatography on silica (EtOAc: $NEt_3$, 99:1 as eluent) to give 130 mg of the desired product 11 (74% yield). $^1$H NMR (200 MHz, $CDCl_3$) 7.76-7.52 (4H, m, ArH), 7.03-6.94 (2H, m, ArH), 6.90-6.81 (1H, m, ArH), 6.76-6.67 (1H, m, ArH), 6.66-6.54 (4H, m, ArH), 6.14-6.03 (1H, m, ArH), 6.03-5.91 (1H, m, ArH), 3.12-2.96 (4H, m, $CH_2$) 3.03 (6H, s, $NCH_3$), 2.95-2.64 (4H, m, $CH_2$), 2.26-1.84 (4H, m, $CH_2$) ppm. EI-MS: m/z calc. $C_{34}H_{32}{}^{191}IrN_7$ 729.2. found 729.2.

Example 12

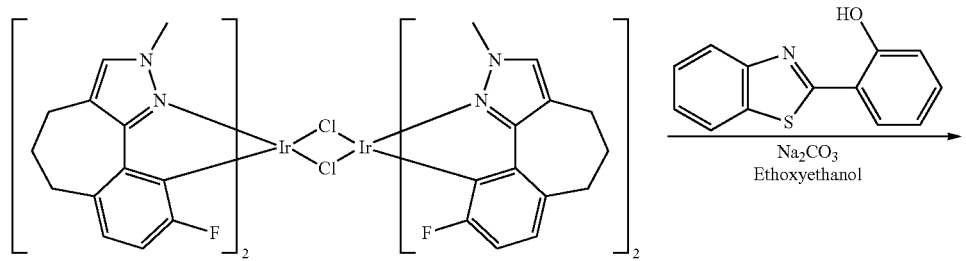

5

Dimer 5 (150 mg, 0.11 mmol), 2-(benzo[d]thiazol-2-yl) phenol (78 mg. 0.34 mmol) and sodium carbonate (121 mg, 1.1 mmol) were dissolved in 20 ml 2-ethoxyethanol. The mixture was degassed with $N_2$ and heated under an atmosphere of nitrogen at an oil bath temperature of 90° C. for ninety minutes. After this time the reaction was complete as indicated by NMR analysis. The solvent was removed under reduced pressure, $CH_2Cl_2$ was added and the excess $Na_2CO_3$ was filtered off. The solvent was removed and the residue was purified by chromatography on silica using EtOAc: hexane mixtures as eluent to give 155 mg of the desired product 12 (80% yield). $^1$H NMR (200 MHz, $CDCl_3$) 7.73-7.59 (1H, m, ArH), 7.57-7.37 (1H, m, ArH), 7.22-6.99 (3H, m, ArH), 6.98-6.80 (3H, m, ArH), 6.64-6.36 (4H, m, ArH), 6.31-5.99 (2H, m, ArH) 3.81 (3H, s, $NCH_3$), 3.35 (3H, s, $NCH_3$) 3.22-2.59 (8H, m, $CH_2$), 2.22-1.76 (4H, m, $CH_2$) ppm. $^{19}$F NMR ($CDCl_3$, 188 MHz) −112.1, −115.4 ppm EI-MS: m/z calc. $C_{39}H_{32}F_2{}^{191}IrN_5OS$ 847.2. found 847.2.

Example 13

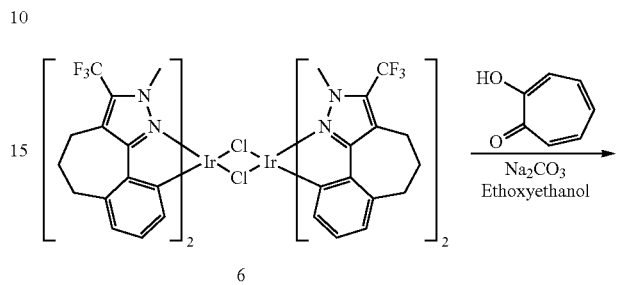

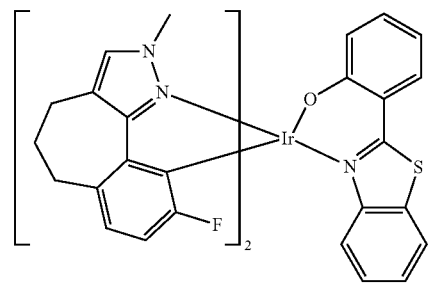

12

-continued

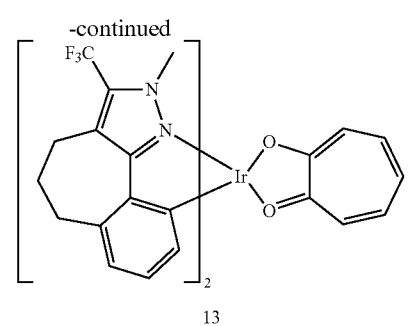

13

Dimer 6 (50 mg, 0.03 mmol), tropolone (10 mg, 0.08 mmol) and sodium carbonate (8.74 mg, 0.08 mmol) were taken up in 2-ethoxyethanol (10 mL) and heated under an atmosphere of nitrogen at an oil bath temperature of 80° C. for 90 minutes. The reaction mixture was allowed to cool to room temperature and the solvent was evaporated. The residue was diluted in CH$_2$Cl$_2$ and filtered through a pad of celite. The crude product was treated with methanol/water (10 mL, 9:1) and the brown precipitate was filtered to give the purified product 13 (50 mg, 72%). $^1$H NMR (200 MHz, CDCl$_3$) 7.34-7.24 (3H, m, CH), 7.12-7.06 (2H, m, CH), 6.58-6.56 (4H, m, ArH), 5.94-5.86 (2H, m, ArH), 3.96 (6H, br s, NCH$_3$), 3.10-2.85 (8H, m, CH$_2$), 2.27-2.16 (2H, m, CHH) 2.05-1.90 (2H, m, CHH). EI-MS: m/z calc. C$_{35}$H$_{29}$F$_6$$^{191}$IrN$_4$O$_2$ 842.2. found 842.3.

Example 14

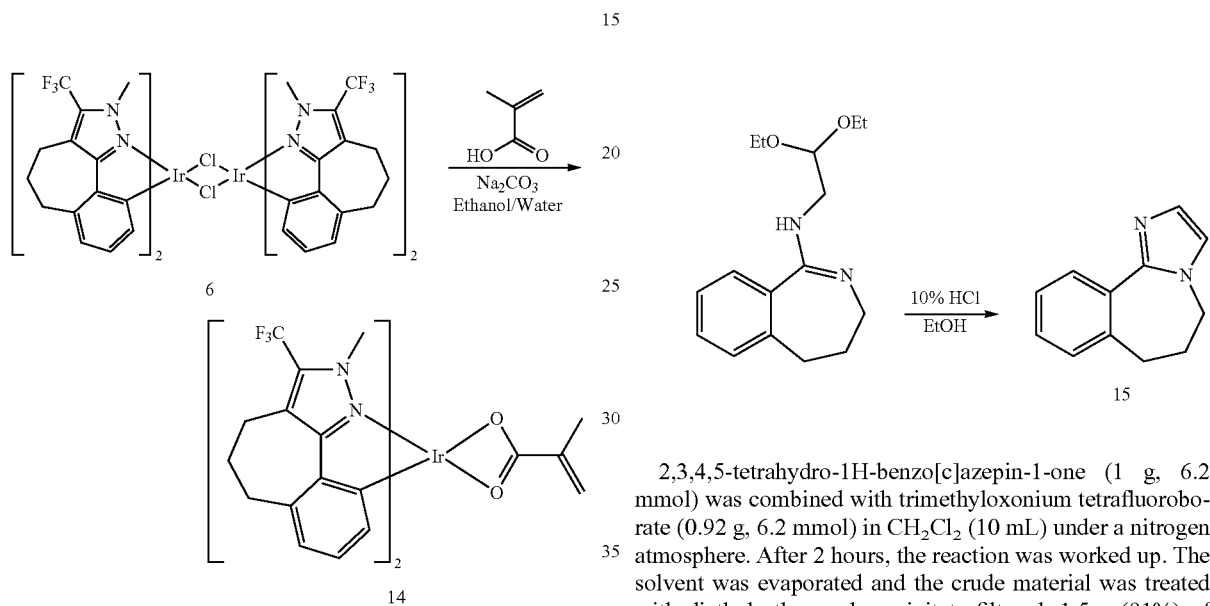

Dimer 6 (100 mg, 0.06 mmol), methacrylic acid (14 µL, 0.16 mmol) and sodium carbonate (17 mg, 0.16 mmol) were taken up in ethanol/water (4:1, 5 mL) and heated under an atmosphere of nitrogen at an oil bath temperature of 90° C. for 90 minutes. The reaction mixture was allowed to cool to room temperature and the solvent was evaporated. The residue was diluted in CH$_2$Cl$_2$ (20 mL) and washed with water (20 mL), saturated NaHCO$_3$ (20 mL) and dried over anhydrous MgSO$_4$. The solvent was evaporated to give the desired product 14 (0.1 g, 75%) as a yellow solid. $^1$H NMR (200 MHz, CDCl$_3$) 6.55-6.50 (4H, m, ArH), 6.04 (1H, br s, CHH), 5.79-5.77 (2H, m, ArH), 5.43 (1H, br s, CHH), 4.17 (6H, br s, NCH$_3$), 3.13-2.91 (8H, m, CH$_2$), 2.23-2.15 (2H, m, CHH) 2.03-1.93 (2H, m, CHH), 1.90 (3H, br s, CH$_3$). EI-MS: m/z calc. C$_{32}$H$_{29}$F$_6$$^{191}$IrN$_4$O$_2$ 808.2. found 808.2.

Example 15

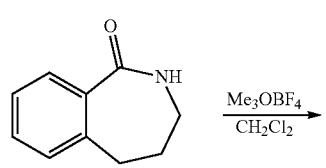

2,3,4,5-tetrahydro-1H-benzo[c]azepin-1-one (1 g, 6.2 mmol) was combined with trimethyloxonium tetrafluoroborate (0.92 g, 6.2 mmol) in CH$_2$Cl$_2$ (10 mL) under a nitrogen atmosphere. After 2 hours, the reaction was worked up. The solvent was evaporated and the crude material was treated with diethyl ether and precipitate filtered. 1.5 g (91%) of 1-methoxy-4,5-dihydro-3H-benzo[c]azepine tetrafluoroborate was isolated as a colourless solid. $^1$H NMR (200 MHz, CDCl$_3$) 7.73-7.64 (2H, m, ArH), 7.53-7.39 (2H, m, ArH) 4.48 (3H, s, OCH$_3$), 3.60 (2H, t, J=6.7 Hz, CH$_2$) 2.91 (2H, t, J=7.3 Hz, CH$_2$), 2.54-2.30 (2H, m, CH$_2$). Without further purification, the 1-methoxy-4,5-dihydro-3H-benzo[c] azepine tetrafluoroborate (0.15 g) was taken up in aminoacetaldehyde diethylacetal (1 mL) and the reaction heated at an oil bath temperature of 100° C. for 1 hour. The reaction was cooled to room temperature and the solvent was evaporated under high vacuum. The crude residue was taken up in 10% HCl(aq)/EtOH (1:1, 10 mL) and heated at reflux for 2 hours. The reaction was allowed to cool to room temperature and the solvent concentrated. The pH was adjusted by the addition of saturated NaHCO$_3$ (50 mL) and the crude product was extracted with CH$_2$Cl$_2$ (2×50 mL), dried over MgSO$_4$ and solvent evaporated under reduced pressure. Purification by chromatography on silica (1:1 EtOAc/hexane) gave 70 mg (66%) of the pure 6,7-dihydro-5H-benzo[c]imidazo[1,2-a]azepine 15. $^1$H NMR (400 MHz, CDCl$_3$), 7.78-7.75 (1H, m, ArH), 7.35-7.28 (2H, m, ArH), 7.22-7.24 (1H, m, ArH), 7.11 (1H, d, J=1.2 Hz, ArH), 6.99 (1H, d, J=1.2 Hz, ArH), 3.90 (2H, t, J=6.7 Hz, CH$_2$), 2.71 (2H, t, J=7.0 Hz, CH$_2$), 2.31 (2H, m, CH$_2$).

Ligand 15 may be reacted with IrCl$_3$ to form a tris heteroleptic complex in a manner outlined in examples 4-14. Alternatively, Ligand 15 may be reacted with other metal reagents derived from Pt, Rh, Pd, Ru or Os.

Example 16

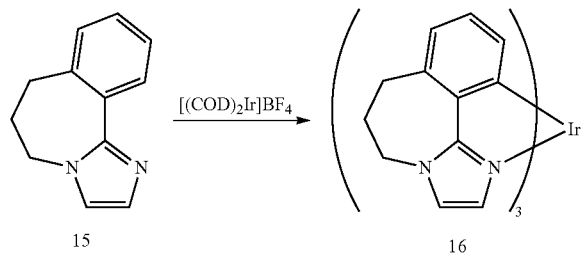

6,7-dihydro-5H-benzo[c]imidazo[1,2-a]azepine 15 (70 mg, 0.38 mmol) was combined with [bis(1,5-cyclopentadiene)iridium(I)]tetrafluoroborate (47 mg, 0.09 mmol) in 1,2-propanediol (1 mL) and freeze pump thaw degassed. The reaction mixture was heated at an oil bath temperature of 180° C. for 18 hours. The reaction was allowed to cool to room temperature and degassed water was added. The yellow precipitate was collected by filtration. The excess free ligand was removed by washing through with methanol leaving the tris(6,7-dihydro-5H-benzo[c]imidazo[1,2-a]azepine-N,$C^2$)iridium (III) 16 as a single fac isomer (determined by a single set of signals in the NMR spectrum indicating a symmetrical isomer). $^1$H NMR (400 MHz, $CD_2Cl_2$) 6.83 (3H, d, J=1.4 Hz, ArH), 6.76-6.74 (3H, m, ArH), 6.60-6.52 (6H, m, ArH), 6.38 (3H, d, J=1.4 Hz, ArH), 4.29-4.19 (6H, m, $CH_2$), 3.17-3.04 (6H, m, $CH_2$), 2.28-2.16 (6H, m, $CH_3$).). EI-MS: m/z calc. $C_{36}H_{33}{}^{191}IrN_6$ 741.9. found 742.2.

Example 17

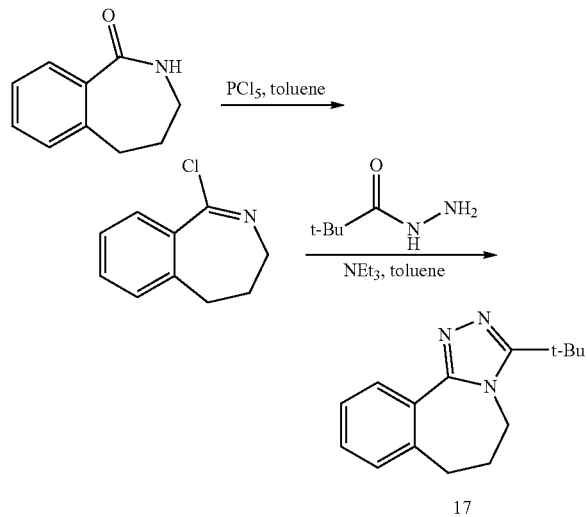

2,3,4,5-tetrahydro-1H-benzo[c]azepin-1-one (0.92 g, 5.7 mmol) was dissolved in toluene (10 ml) and $PCl_5$ (1.188 g, 5.7 mmol) was added. The reaction mixture was heated at an oil bath temperature of 120° C. for 1 hour. The reaction was then cooled to room temperature and concentrated to dryness under vacuum. The residue was redissolved in toluene (10 mL) and re-evaporated to ensure removal of all $POCl_3$ by-product. The crude residue was then taken up in toluene (20 mL), triethylamine (0.95 ml, 6.85 mmol) and pivalohydrazide (0.729 g, 6.28 mmol) were added and the reaction mixture heated at reflux for 3 hours. Tlc analysis showed the presence of the desired product. The reaction was cooled to room temperature and diluted with EtOAc (30 mL). The organic phase was then washed with aqueous NaOH (2N, 20 mL). The product was extracted from the organic phase by washing with 10% aqueous HCl (2×20 mL). The pH of the aqueous phase was adjusted to pH 11 with 2 N NaOH and the product was extracted into $CHCl_3$ (100 mL). The organic phase was dried over $MgSO_4$ and the solvent was evaporated under reduced pressure. A pale brown solid was obtained which could be purified by chromatography on silica (60% EtOAc increasing to 80% EtOAc in hexane) to give 17 as an off white solid (0.97 g, 70% yield). $^1$H NMR (200 MHz, $CDCl_3$) 7.84-7.76 (1H, m, ArH), 7.42-7.37 (2H, m, ArH), 7.29-7.25 (1H, m, ArH), 4.00 (2H, t, $J_1$=6.6 Hz, $CH_2$), 2.69 (2H, t, $J_2$=7.1 Hz, $CH_2$), 2.28 (2H, tt, $J_1$=6.6H, $J_2$=7.1 Hz, $CH_2$), 1.52 (9H, s, tBu).

Ligand 17 may be reacted with Ir to form a tris heteroleptic or homoleptic complex in a manner outlined in examples 4-16. Alternatively, Ligand 17 may be reacted with other metal reagents derived from Pt, Rh, Pd, Ru or Os.

Example 18

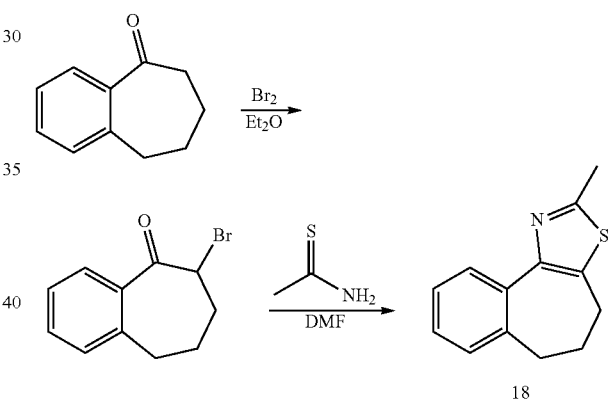

Bromine (1.59 g, 0.5 ml) was added dropwise over 30 minutes to a solution of 6,7,8,9-tetrahydro-5H-benzo[7]annulen-5-one (1.6 g, 10.0 mmol) in diethyl ether (20 ml) at 0° C. The solution was allowed to stir overnight coming slowly to room temperature. The reaction was then diluted with diethyl ether (150 ml) and transferred to a separatory funnel. The organic phase was washed with aqueous thiosulphate (2×100 mL) and water (2×100 mL), dried over $MgSO_4$ and solvent removed under reduced pressure to give 2.47 g crude pale yellow liquid which was purified by chromatography on silica (gradient elution from 100% petroleum spirits (40-60) to 8:2 Petroleum Spirits: DCM) to give 6-bromo-6,7,8,9-tetrahydro-5H-benzo[7]annulene-5-one (2.69 g, 48%) as a pale yellow liquid. $^1$H NMR (400 MHz, $CDCl_3$) δ 7.58 (1H, d, J=7.6 Hz, ArH), 7.40 (1H, t, J=7.5 Hz, ArH), 7.28 (1H, t, J=7.6 Hz, ArH), 7.18 (1H, d, J=7.6 Hz, ArH), 4.86-4.84 (1H, m, CHH), 3.05-2.98 (1H, m, CHH), 2.92-2.85 (1H, m, CHH), 2.41-2.35 (1H, m, CHH), 2.31-2.25 (1H, m, CHH), 2.05-1.97 (2H, m, CHH). 6-bromo-6,7,8,9-tetrahydro-5H-benzo[7]annulen-5-one (239 mg, 1.0 mmol) and thioacetamide (100 mg, 1.3 mmol) were heated in DMF (10 ml) at an oil bath temperature of 80° C. for 33 hours. After this time the solution was cooled to room temperature and the solvent removed in vacuo. The crude residue was diluted with $CH_2Cl_2$ (150 mL) and washed with saturated aqueous $NaHCO_3$ (50 mL) and water (2×50 mL), dried over $MgSO_4$ and the solvent evaporated to give a crude orange oil. Purification by chromatography on silica (gradient elution of 100% $CH_2Cl_2$ to 9:1 $CH_2Cl_2$: EtOAc) gave 18 as clear, colourless oil. $^1H$ NMR (400 MHz, $CDCl_3$) δ 7.97-7.95 (1H, d, Aril), 7.29-7.26 (1H, m, ArH), 7.21-7.16 (2H, m, ArH), 2.94-2.86 (2H, m, $CH_2$) 2.77-2.74 (2H, m, $CH_2$), 2.68 (3H, s, $CH_3$), 2.20-2.14 (2H, m, $CH_2$).

Ligand 18 may be reacted with Ir to form a tris heteroleptic or homoleptic complex in a manner outlined in examples 4-16. Alternatively, Ligand 18 may be reacted with other metal reagents derived from Pt, Rh, Pd, Ru or Os.

Example 19

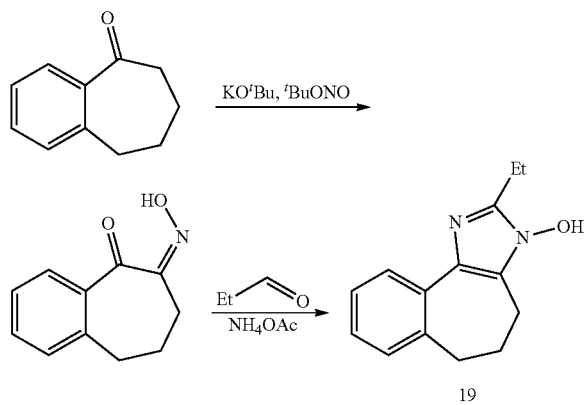

Potassium tert-butoxide (2.5 g, 22.2 mmol) was taken up in ethanol (25 ml) and the mixture stirred at room temperature for 30 min. of 6,7,8,9-tetrahydro-5H-benzo[7]annulen-5-one (1.0 g, 6.25 mmol) was then added, and the mixture allowed to stir a further 30 minutes at room temperature. Tert-butyl nitrite (1.35 g, 13.1 mmol) was added dropwise and the resulting solution stirred overnight at room temperature. The reaction was diluted with water (25 mL), and the reddish solution acidified (pH 1-3) with concentrated HCl. The acidic mixture was then extracted with diethyl ether, and separated, dried over $MgSO_4$ and the solvent evaporated to give a crude solid. Purification by chromatography on silica (gradient elution, 100% petroleum spirits (40-60) to 100% DCM to a 9:1 mixture of DCM: EtOAc) gave the 6-(hydroxyimino)-6,7,8,9-tetrahydro-5H-benzo[7]annulen-5-one as a pale tan solid (0.56 g, 48%) (Hydroxyimino)-6,7,8,9-tetrahydro-5H-benzo[7]annulen-5-one (567 mg, 3.0 mmol), ammonium acetate (900 mg, 11.6 mmol), and propionaldehyde (0.22 ml, 3.0 mmol) were stirred in acetic acid (30 ml) at room temperature until TLC analysis indicated the ketoxime had been consumed. The acetic acid was then removed by evaporation under reduced pressure. The crude residue was diluted in 300 ml DCM. The organic phase was then washed with saturated $NaHCO_3$ (150 mL), water (2×150 mL) and dried over anhydrous $MgSO_4$. Removal of the solvent under reduced pressure gave 480 mg of crude material as a dark brownish oil. Purification by chromatography on silica (gradient elution of 100% DCM to 95 DCM, 5% MeOH) gave the N-hydroxy-imidazole 19 (260 mg, 40%) as a pale brown oil. $^1H$ NMR (400 MHz, $CDCl_3$) δ 8.96 (1H, br s, OH), 7.67-7.66 (1H, m, ArH), 7.04-6.96 (3H, m, ArH), 2.77-2.74 (2H, m, $CH_2$), 2.69-2.67 (2H, m, $CH_2$), 2.68-2.58 (2H, q, J=7.6 Hz, $CH_2$), 1.89-1.84 (2H, m, $CH_2$), 1.04-1.00 (3H, t, J=7.6 Hz, $CH_3$).

Ligand 19 may be reacted with Ir to form a tris heteroleptic or homoleptic complex in a manner outlined in examples 4-16. Alternatively, Ligand 19 may be reacted with other metal reagents derived from Pt, Rh, Pd, Ru or Os.

Example 20

An organic electroluminescent device was fabricated in the following manner:

An ITO patterned glass substrate was successively sonicated in acetone and iso-propanol for 15 minutes and dried. Then PEDOT:PSS was spin coated on top of the ITO at a spin-speed of 4000 rpm for 1 min and baked on hot plate at 150° C. for 15 min. The thickness of the PEDOT:PSS layer was determined to be 40 nm. After this the substrate was transferred into a glove box and an emission layer was spin coated on top of the PEDOT:PSS layer at a spin-speed of 3000 rpm for 1 min and baked at 80° C. for 30 min. A solution consisting of PVK, PBD, TPD and compound 10, dissolved in chlorobenzene, was used to form the emission layer. The weight ratio of the four components was 65:25:9:6. The thickness of the emission layer was determined to be 90 nm. Then layers of TPBi (hole blocking layer, 20 nm), LiF (electron injection layer, 1 nm) and Al (cathode, 120 nm) were subsequently deposited under a vacuum of $1 \times 10^{-5}$ Pa.

When a voltage was applied between the anode and the cathode, the device emitted light with a maximum wavelength of 565 nm. The CIE colour coordinates were (0.49; 0.49). The maximum current efficiency was 20 cd/A at a brightness of 1800 $cd/m^2$ and a voltage of 15 V. The maximum brightness was 20000 $cd/m^2$ at 21 V.

This example clearly demonstrates that when a phosphorescent material disclosed herein is included in an organic electroluminescent device disclosed herein, the device emits light (see also FIG. 5).

It is to be understood that referring herein to any prior art publication does not constitute an admission that the publication forms a part of the common general knowledge in the art, in Australia or any other country.

In the claims which follow and in the preceding description of the invention, except where the context requires otherwise due to express language or necessary implication, the word "comprise" or variations such as "comprises" or "comprising" is used in an inclusive sense, i.e. to specify the presence of the stated features but not to preclude the presence or addition of further features in various embodiments of the invention.

The invention claimed is:
1. An organic electroluminescent device comprising:
a pair of electrodes comprising an anode and a cathode, and
one or more layers of organic compound arranged between the anode and the cathode, wherein at least one of the one or more layers of organic compound comprises a phosphorescent material; wherein the phosphorescent material comprises a complex of a metal atom M selected from Ir, Pt, Rh, Pd, Ru and Os and at least one ligand L, wherein the ligand L is represented by formula (1):

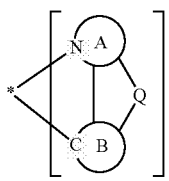

(1)

wherein:
- ring A is a substituted or unsubstituted 5-membered heterocycle containing at least one ring nitrogen atom bound to the metal atom at the asterisk (*), wherein ring A may be substituted with one or more substituents selected from the group consisting of:
  halogen, cyano, amide, imine, imide, amidine, amine, nitro, hydroxy, ether, carbonyl, carboxy, carbonate, carbamate, phosphine, phosphate, phosphonate, sulphide, sulphone, sulphoxide, silyl, substituents containing a functional group that can be polymerised or a polymer chain, substituted or unsubstituted alkyl, substituted or unsubstituted alkenyl, and substituted or unsubstituted alkynyl, wherein:
    one or more of the carbon atoms in the alkyl may be replaced, wherein each carbon atom that is replaced is independently replaced with an atom or group selected from the group consisting of: —C(=O)—, —O—, —S—, —N', —C=N—, —Si— and —P—;
- ring B is a substituted or unsubstituted 5- or 6-membered carbocycle or heterocycle containing a carbon atom as represented in formula (1) which is bound to the metal atom at the asterisk (*),
- rings A and B are joined by a direct covalent bond as represented in formula (1),
- rings A and B are joined via a tether Q, wherein
- Q is a tether of between 3 and 20 atoms in length, and is selected from the group consisting of: linear, branched or cyclic alkyl; linear or branched alkenyl; linear or branched alkynyl; aryl; and alkyl-aryl; wherein one or more of the carbon atoms in the alkyl, aryl or alkyl-aryl may be replaced, wherein each carbon atom that is replaced is independently replaced with an atom or group selected from the group consisting of: —C(=O)—, —O—, —S—, —N—, =N—, —Si— and —P—; wherein when the atom is =N—, the nitrogen double bond is to an adjacent carbon atom in the alkyl, aryl, or alkyl-aryl so as to form a —C=N— group; and wherein the tether may contain one or more substituents selected from the group consisting of halogen, cyano, amide, imine, imide, amidine, amine, nitro, hydroxy, ether, carbonyl, carboxy, carbonate, carbamate, phosphine, phosphate, phosphonate, sulphide, sulphone, sulphoxide, alkenyl, aryl, alkyl, heteroaryl, alkynyl, silyl, and substituents containing a functional group that can be polymerised, a polymer chain, or two substituents may together form a ring or fused ring system.

2. The device of claim 1, wherein ring B may be substituted with one or more substituents selected from the group consisting of:
halogen, cyano, amide, imine, imide, amidine, amine, nitro, hydroxy, ether, carbonyl, carboxy, carbonate, carbamate, phosphine, phosphate, phosphonate, sulphide, sulphone, sulphoxide, silyl, substituents containing a functional group that can be polymerised or a polymer chain, substituted or unsubstituted alkyl, substituted or unsubstituted alkenyl, substituted or unsubstituted alkynyl, substituted or unsubstituted aryl and substituted or unsubstituted alkyl-aryl, wherein:
  one or more of the carbon atoms in the alkyl, aryl or alkyl-aryl may be replaced wherein each carbon atom that is replaced is independently replaced with an atom or group selected from the group consisting of: —C(=O)—, —O—, —S—, —N—, —C=N—, —Si— and —P—,
  the substituents on the alkyl, aryl or alkyl-aryl are selected from the group consisting of: halogen, cyano, amide, imine, imide, amidine, amine, nitro, hydroxy, ether, carbonyl, carboxy, carbonate, carbamate, phosphine, phosphate, phosphonate, sulphide, sulphone, sulphoxide, alkenyl, alkynyl, silyl, and substituents containing a functional group that can be polymerised or a polymer chain, and
  the alkyl, aryl or alkyl-aryl may additionally be connected to the tether Q, or the alkyl, aryl or alkyl-aryl may be attached via two points to its core ring B to form a fused ring or ring system.

3. The device of claim 1, wherein the phosphorescent material comprises 1, 2 or 3 ligands L of formula (1), and 0, 1 or 2 bidentate ligands L' of a different identity to ligand L.

4. The device of claim 3, wherein the ligand L' of the phosphorescent material is a ligand of formula (5), a ligand of formula (6) or a ligand of formula (7):

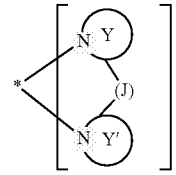

(5)

wherein:
- ring Y is a 5-, 6- or 7-membered heterocycle which is unsubstituted or substituted by one or more substituents, containing at least one nitrogen atom as represented in the formula, which is bound to the metal atom at the asterisk (*),
- ring Y' is a 5-, 6- or 7-membered heterocycle which is unsubstituted or substituted by one or more substituents, and containing at least one nitrogen atom as represented in the formula which is bound to the metal atom at the asterisk (*), and
- rings Y and Y' are either joined by a direct covalent bond or via a linker J as represented in formula (5), wherein J, when present, is a B, C, O, N, P, Si or S atom which is covalently bonded to both rings Y and Y' and which may be substituted or unsubstituted depending on its valency;

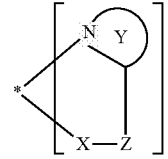

(6)

wherein:
ring Y is as defined in formula (5),
Z is a ligand component connected via a covalent bond to ring Y, and connected to the metal atom via X, and
X is an N, O, S or P atom bound to the metal atom at the asterisk (*), wherein the N or P atom is unsubstituted or is substituted

 (7)

wherein
G is a ligand component consisting of one or two substituted or unsubstituted carbon atoms in length, which is connected covalently to two O atoms, and
the O atoms are each bound to the metal atom at the asterisk (*).

5. The device of claim 1, wherein ligand L of the phosphorescent material is of the formula (3):

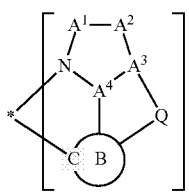 (3)

wherein:
$A^1$ and $A^2$ are each independently selected from the group consisting of: C, N, O and S, wherein the C or N may be substituted or unsubstituted,
$A^3$ and $A^4$ are selected from the group consisting of: C and N, wherein the C may be substituted or unsubstituted.

6. The device of claim 5, wherein the ligand L of the phosphorescent material is of the formula (4):

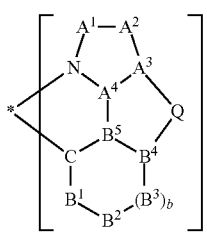 (4)

wherein:
$B^1$ and $B^2$ are each independently selected from the group consisting of: C, N, O and S, wherein the C or N may be substituted or unsubstituted,
$B^3$, when present, is selected from the group consisting of: C, N, O and S, wherein the C or N may be substituted or unsubstituted,
b is 0 or 1,
$B^4$ is selected from the group consisting of: C and N, wherein the C may be substituted or unsubstituted, and
$B^5$ is C.

7. The device of claim 6, wherein the ligand L of the phosphorescent material is selected from the group consisting of:

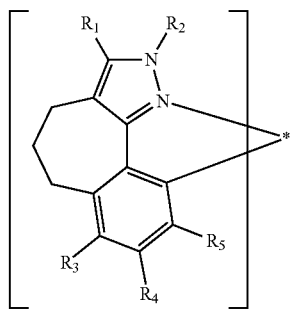

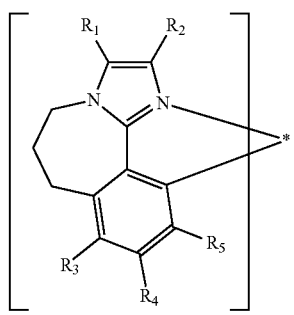

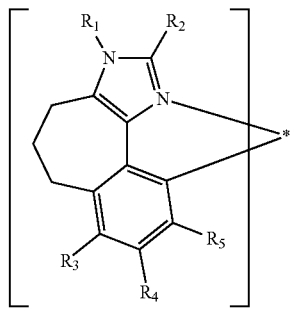

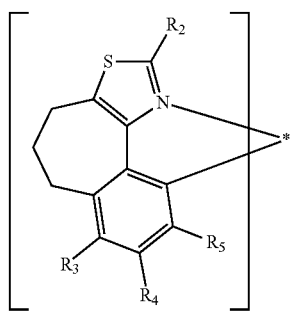

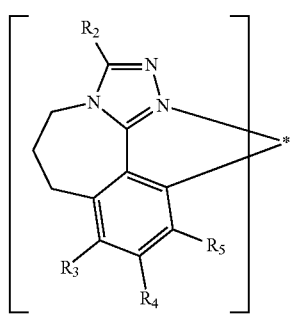

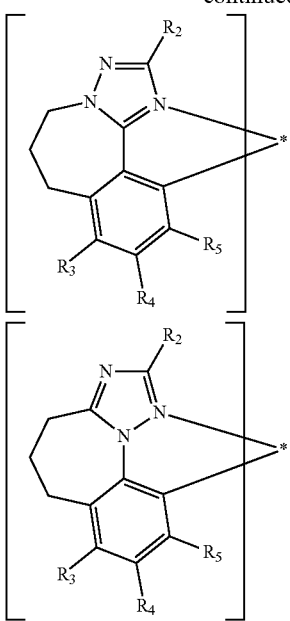

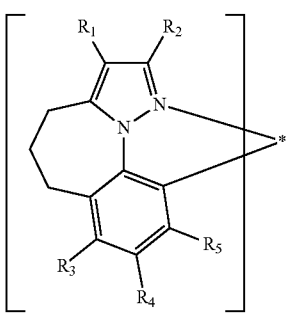

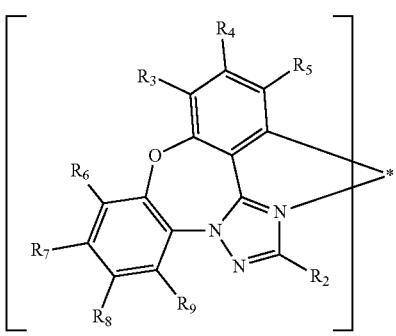

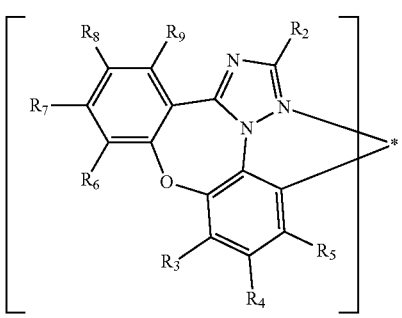

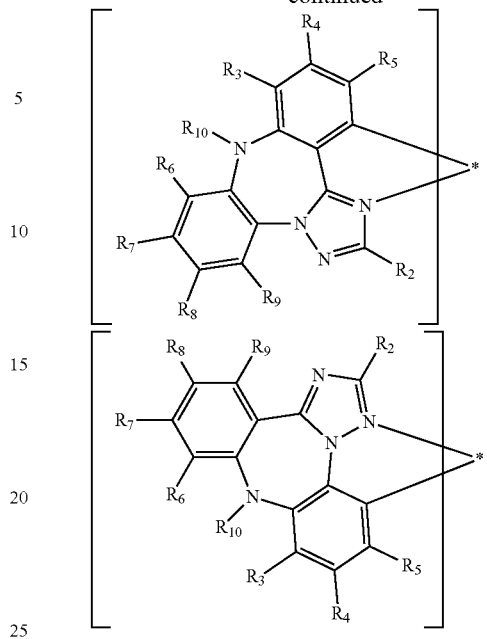

wherein:
$R_1$ and $R_2$ are independently selected from the group consisting of:
hydrogen, halogen, cyano, amide, imine, imide, amidine, amine, nitro, hydroxy, ether, carbonyl, carboxy, carbonate, carbamate, phosphine, phosphate, phosphonate, sulphide, sulphone, sulphoxide, silyl, substituents containing a functional group that can be polymerised or a polymer chain, substituted or unsubstituted alkyl, substituted or unsubstituted alkenyl, and substituted or unsubstituted alkynyl wherein:
one or more of the carbon atoms in the alkyl may be replaced, wherein each carbon atom that is replaced is independently replaced with an atom or group selected from the group consisting of: —C(=O)—, —O—, —S—, —N—, —C=N—, —Si— and —P—;
the substituents on the alkyl are selected from the group consisting of: halogen, cyano, amide, imine, imide, amidine, amine, nitro, hydroxy, ether, carbonyl, carboxy, carbonate, carbamate, phosphine, phosphate, phosphonate, sulphide, sulphone, sulphoxide, alkenyl, alkynyl, silyl, and substituents containing a functional group that can be polymerised or a polymer chain;
$R_3$, $R_4$, and $R_5$ are independently selected from the group consisting of:
hydrogen, halogen, cyano, amide, imine, imide, amidine, amine, nitro, hydroxy, ether, carbonyl, carboxy, carbonate, carbamate, phosphine, phosphate, phosphonate, sulphide, sulphone, sulphoxide, silyl, and substituents containing a functional group that can be polymerised or a polymer chain, substituted or unsubstituted alkyl, substituted or unsubstituted alkenyl, substituted or unsubstituted alkynyl, substituted or unsubstituted aryl and substituted or unsubstituted alkyl-aryl, wherein:
one or more of the carbon atoms in the alkyl, aryl or alkyl-aryl may be replaced, wherein each carbon atom that is replaced is independently replaced with an atom or group selected from the group consisting of: —C(=O)—, —O—, —S—, —N—, —C=N—, —Si— and —P—;

the substituents on the alkyl, aryl or alkyl-aryl are selected from the group consisting of: halogen, cyano, amide, imine, imide, amidine, amine, nitro, hydroxy, ether, carbonyl, carboxy, carbonate, carbamate, phosphine, phosphate, phosphonate, sulphide, sulphone, sulphoxide, alkenyl, alkynyl, silyl, and substituents containing a functional group that can be polymerised or a polymer chain;

$R_6$, $R_7$, $R_8$, $R_9$ and $R_{10}$ are independently selected from the group consisting of:

hydrogen, halogen, cyano, amide, imine, imide, amidine, amine, nitro, hydroxy, ether, carbonyl, carboxy, carbonate, carbamate, phosphine, phosphate, phosphonate, sulphide, sulphone, sulphoxide, alkenyl, aryl, alkyl, heteroaryl, alkynyl, silyl, and substituents containing a functional group that can be polymerised, a polymer chain, or two substituents may together form a ring or fused ring system.

8. The device of claim 1, wherein the phosphorescent material is of formula (2):

and wherein:
L' is a bidentate ligand of a different identity to L,
m is an integer selected from 1, 2 and 3, and
n is an integer selected from 0, 1 and 2.

9. A phosphorescent material comprising a complex of a metal atom M selected from Ir, Pt, Rh, Pd, Ru and Os and at least one ligand L, wherein the ligand L is represented by formula (1):

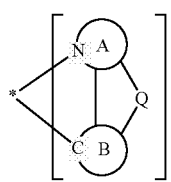

(1)

wherein:
ring A is a substituted or unsubstituted 5-membered heterocycle containing at least one ring nitrogen atom bound to the metal atom at the asterisk (*); wherein ring A may be substituted with one or more substituents from the group consisting of:
halogen, cyano, amide, imine, imide, amidine, amine, nitro, hydroxy, ether, carbonyl, carboxy, carbonate, carbamate, phosphine, phosphate, phosphonate, sulphide, sulphone, sulphoxide, silyl, substituents containing a functional group that can be polymerised or a polymer chain, substituted or unsubstituted alkyl, substituted or unsubstituted alkenyl, and substituted or unsubstituted alkynyl wherein:
one or more of the carbon atoms in the alkyl may be replaced, wherein each carbon atom that is replaced is independently replaced with an atom or group selected from the group consisting of: —C(=O)—, —O—, —S—, —N—, —C=N—, —Si— and —P—;

ring B is a substituted or unsubstituted 5- or 6-membered carbocycle or heterocycle containing a carbon atom as represented in formula (1) which is bound to the metal atom at the asterisk (*),
rings A and B are joined by a direct covalent bond as represented in formula (1),
rings A and B are joined via a tether Q, wherein
Q is a tether of between 3 and 30 atoms in length, and is selected from the group consisting of: linear, branched, or cyclic alkyl; linear or branched alkenyl; linear or branched alkynyl; aryl; alkyl-aryl, wherein one or more of the carbon atoms in the alkyl, aryl or alkyl-aryl may be replaced, wherein each carbon atom that is replaced is independently replaced with an atom or group selected from: —C(=O)—, —O—, —S—, —N—, =N—, —Si— and —P—, wherein when the atom is =N—, the nitrogen double bond is to an adjacent carbon atom in the alkyl, aryl, or alkyl-aryl so as to form a —C=N— group; and wherein the tether may contain one or more substituents selected from the group consisting of: halogen, cyano, amide, imine, imide, amidine, amine, nitro, hydroxy, ether, carbonyl, carboxy, carbonate, carbamate, phosphine, phosphate, phosphonate, sulphide, sulphone, sulphoxide, alkenyl, aryl, alkyl, heteroaryl, alkynyl, silyl, and substituents containing a functional group that can be polymerised, a polymer chain, or two substituents may together form a ring or fused ring system.

10. The phosphorescent material of claim 9 having the formula

wherein:
L' is a bidentate ligand of a different identity to L,
m is an integer selected from 1, 2 and 3, and
n is an integer selected from 0, 1 and 2.

11. The phosphorescent material of claim 10, wherein m+n=2 or 3.

12. The phosphorescent material of claim 10, wherein the ligand L' is a ligand of formula (5), a ligand of formula (6) or a ligand of formula (7):

(5)

wherein:
ring Y is a 5-, 6- or 7-membered heterocycle which is unsubstituted or substituted by one or more substituents, containing at least one nitrogen atom as represented in the formula, which is bound to the metal atom at the asterisk (*),
ring Y' is a 5-, 6- or 7-membered heterocycle which is unsubstituted or substituted by one or more substituents, and containing at least one nitrogen atom as represented in the formula which is bound to the metal atom at the asterisk (*), and
rings Y and Y' are either joined by a direct covalent bond or via a linker J as represented in formula (5), wherein J, when present, is a B, C, O, N, P, Si or S atom which is covalently bonded to both rings Y and Y' and which may be substituted or unsubstituted depending on its valency;

(6)

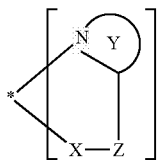

wherein:

ring Y is as defined in formula (5),

Z is a ligand component connected via a covalent bond to ring Y, and connected to the metal atom via X, and X is an N, O, S or P atom bound to the metal M at the asterisk (*), wherein the N or P atom is unsubstituted or is substituted;

(7)

[diagram of formula 7]

wherein:

G is a ligand component consisting of one or two substituted or unsubstituted carbon atoms in length, which is connected covalently to two O atoms, and the O atoms are each bound to the metal at the asterisk (*).

13. The phosphorescent material of claim 12, wherein the ligand L of the phosphorescent material is selected from the group consisting of:

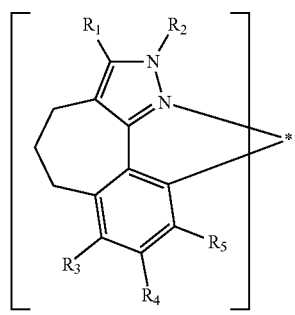

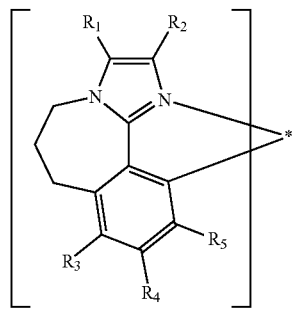

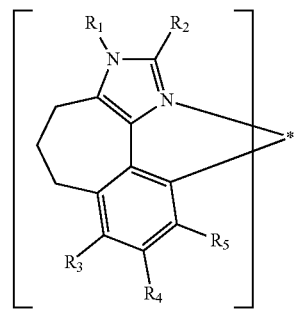

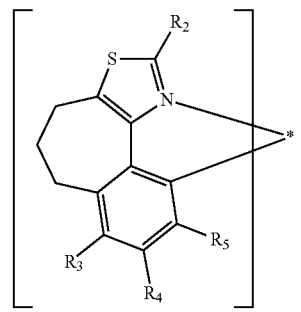

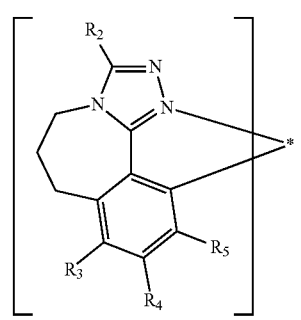

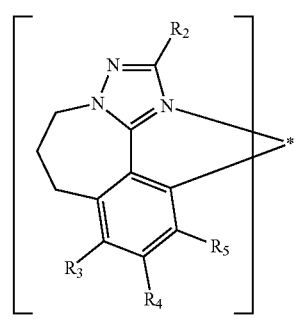

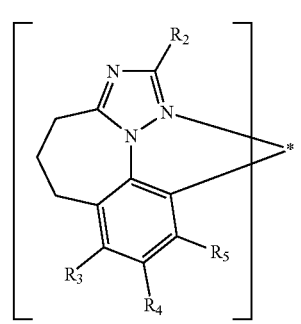

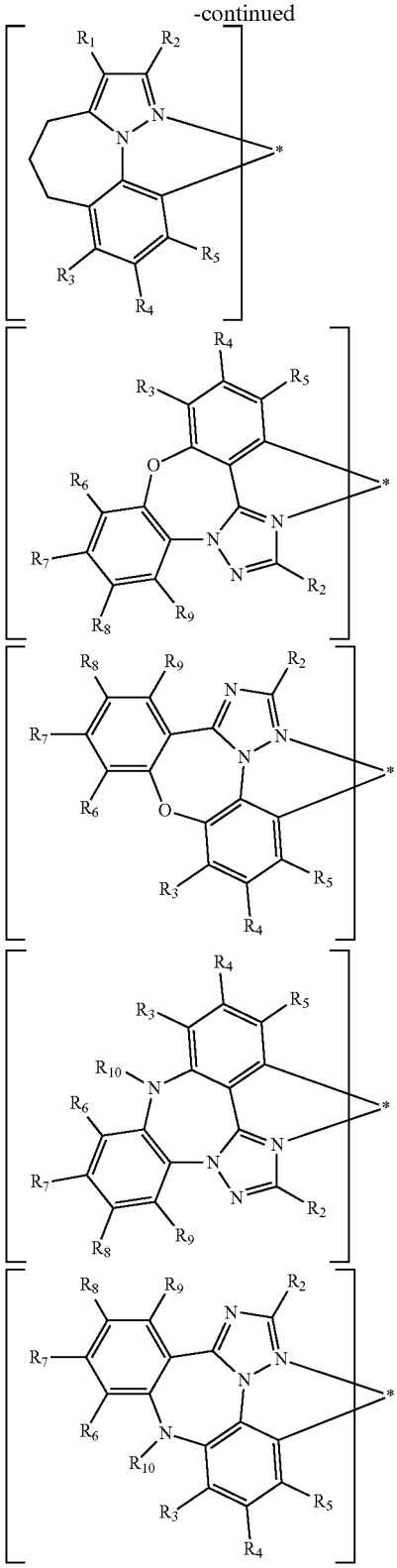

wherein:

R$_1$ and R$_2$ are independently selected from the group consisting of:
  hydrogen, halogen, cyano, amide, imine, imide, amidine, amine, nitro, hydroxy, ether, carbonyl, carboxy, carbonate, carbamate, phosphine, phosphate, phosphonate, sulphide, sulphone, sulphoxide, silyl, substituents containing a functional group that can be polymerised or a polymer chain, substituted or unsubstituted alkyl, substituted or unsubstituted alkenyl, and substituted or unsubstituted alkynyl, wherein:
  one or more of the carbon atoms in the alkyl may be replaced, wherein each carbon atom that is replaced is independently replaced with an atom or group selected from the group consisting of: —C(=O)—, —O—, —S—, —N—, —C=N—, —Si— and —P—;
  the substituents on the alkyl are selected from the group consisting of: halogen, cyano, amide, imine, imide, amidine, amine, nitro, hydroxy, ether, carbonyl, carboxy, carbonate, carbamate, phosphine, phosphate, phosphonate, sulphide, sulphone, sulphoxide, alkenyl, alkynyl, silyl, and substituents containing a functional group that can be polymerised or a polymer chain;

R$_3$, R$_4$, and R$_5$, are independently selected from the group consisting of:
  hydrogen, halogen, cyano, amide, imine, imide, amidine, amine, nitro, hydroxy, ether, carbonyl, carboxy, carbonate, carbamate, phosphine, phosphate, phosphonate, sulphide, sulphone, sulphoxide, silyl, substituents containing a functional group that can be polymerised or a polymer chain, substituted or unsubstituted alkyl, substituted or unsubstituted alkenyl, substituted or unsubstituted alkynyl, substituted or unsubstituted aryl and substituted or unsubstituted alkyl-aryl, wherein:
  one or more of the carbon atoms in the alkyl, aryl or alkyl-aryl may be replaced, wherein each carbon atom that is replaced is independently replaced with an atom or group selected from the group consisting of: —C(=O)—, —O—, —S—, —N—, —C=N—, —Si— and —P—, wherein the atoms —Si— and —P— contain substituents based on their valency;
  the substituents on the alkyl, aryl or alkyl-aryl are selected from the group consisting of: halogen, cyano, amide, imine, imide, amidine, amine, nitro, hydroxy, ether, carbonyl, carboxy, carbonate, carbamate, phosphine, phosphate, phosphonate, sulphide, sulphone, sulphoxide, alkenyl, alkynyl, silyl and substituents containing a functional group that can be polymerised or a polymer chain;

R$_6$, R$_7$, R$_8$, R$_9$ and R$_{10}$ are independently selected from the group consisting of:
  hydrogen, halogen, cyano, amide, imine, imide, amidine, amine, nitro, hydroxy, ether, carbonyl, carboxy, carbonate, carbamate, phosphine, phosphate, phosphonate, sulphide, sulphone, sulphoxide, alkenyl, aryl, alkyl, heteroaryl, alkynyl, silyl, and substituents containing a functional group that can be polymerised, a polymer chain, or two substituents may together form a ring or fused ring system.

14. A method for the production of a phosphorescent material comprising:
  reacting a precursor complex of a metal M, with a ligand L, in a ratio suitable to result in a product containing the desired number of ligands L being co-ordinated to the metal M, optionally followed by:
  reacting the product with another ligand L' in a ratio suitable to introduce the desired number of ligands L' into the product, wherein:

M is a metal atom selected from Ir, Pt, Rh, Pd, Ru and Os,

L is a ligand represented by formula (1):

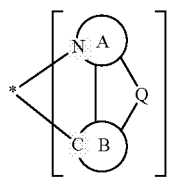

(1)

wherein:
- ring A is a substituted or unsubstituted 5-membered heterocycle containing at least one ring nitrogen atom bound to the metal atom at the asterisk (*); wherein ring A may be substituted with one or more substituent selected from the group consisting of: halogen, cyano, amide, imine, imide, amidine, amine, nitro, hydroxy, ether, carbonyl, carboxy, carbonate, carbamate, phosphine, phosphate, phosphonate, sulphide, sulphone, sulphoxide, silyl, substituents containing a functional group that can be polymerised or a polymer chain, substituted or unsubstituted alkyl, substituted or unsubstituted alkenyl, and substituted or unsubstituted alkynyl, wherein:
  - one or more of the carbon atoms in the alkyl may be replaced wherein each carbon atom that is replaced is independently replaced with an atom selected from the group consisting of: —C(═O)—, —O—, —S—, —N—, —C═N—, —Si— and —P—;
- ring B is a substituted or unsubstituted 5- or 6-membered carbocycle or heterocycle containing a carbon atom as represented in formula (1) which can bind to the metal atom at the asterisk (*),
- rings A and B are joined by a direct covalent bond as represented in formula (1),
- rings A and B are joined via a tether Q, wherein
- Q is a tether of between 3 and 20 atoms in length, and is selected from the group consisting of: linear, branched, or cyclic alkyl; linear or branched alkenyl; linear or branched alkynyl; aryl alkyl-aryl; wherein one or more of the carbon atoms in the alkyl, aryl or alkyl-aryl may be replaced, wherein each carbon atom that is replaced is independently replaced with an atom or group selected from: —C(═O), —O—, —S—, —N—, ═N—, —Si— and —P—, wherein when the atom is ═N—, the nitrogen double bond is to an adjacent carbon atom in the alkyl, aryl, or alkyl-aryl so as to form a —C═N— group; and wherein the tether may contain one or more substituents selected from the group consisting of halogen, cyano, amide, imine, imide, amidine, amine, nitro, hydroxy, ether, carbonyl, carboxy, carbonate, carbamate, phosphine, phosphate, phosphonate, sulphide, sulphone, sulphoxide, alkenyl, aryl, alkyl, heteroaryl, alkynyl, silyl, and substituents containing a functional group that can be polymerised, a polymer chain, or two substituents may together form a ring or fused ring system, and
- L' is a bidentate ligand of a different identity to L.

15. An organic electroluminescent device comprising the phosphorescent material of claim 9.

16. The organic electroluminescent device of claim 1, wherein ring A may be substituted with a substituted or unsubstituted alkyl; wherein the substituents on the alkyl are selected from the group consisting of: halogen, cyano, amide, imine, imide, amidine, amine, nitro, hydroxy, ether, carbonyl, carboxy, carbonate, carbamate, phosphine, phosphate, phosphonate, sulphide, sulphone, sulphoxide, alkenyl, alkynyl, silyl, and substituents containing a functional group that can be polymerised or a polymer chain.

17. The phosphorescent material of claim 9, wherein ring A may be substituted with a substituted or unsubstituted alkyl; wherein the substituents on the alkyl are selected from the group consisting of: halogen, cyano, amide, imine, imide, amidine, amine, nitro, hydroxy, ether, carbonyl, carboxy, carbonate, carbamate, phosphine, phosphate, phosphonate, sulphide, sulphone, sulphoxide, alkenyl, alkynyl, silyl, and substituents containing a functional group that can be polymerised or a polymer chain.

18. The method of claim 14, wherein ring A may be substituted with a substituted or unsubstituted alkyl; wherein the substituents on the alkyl are selected from the group consisting of: halogen, cyano, amide, imine, imide, amidine, amine, nitro, hydroxy, ether, carbonyl, carboxy, carbonate, carbamate, phosphine, phosphate, phosphonate, sulphide, sulphone, sulphoxide, alkenyl, alkynyl, silyl, and substituents containing a functional group that can be polymerised or a polymer chain.

19. The organic electroluminescent device of claim 1, wherein ligand L is selected from:

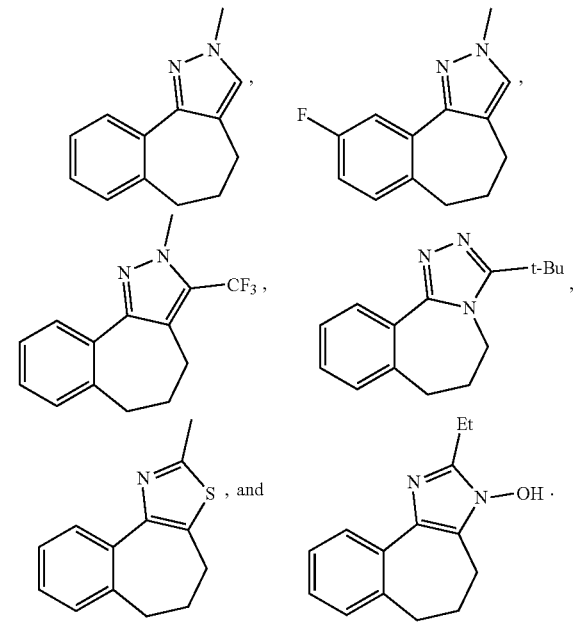

20. The phosphorescent material of claim 9, wherein ligand L is selected from:

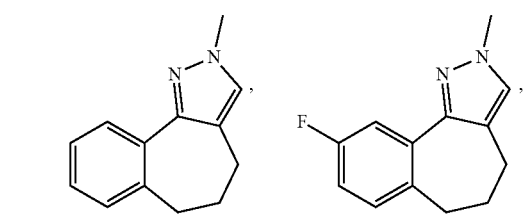

-continued
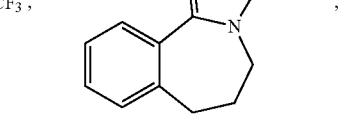
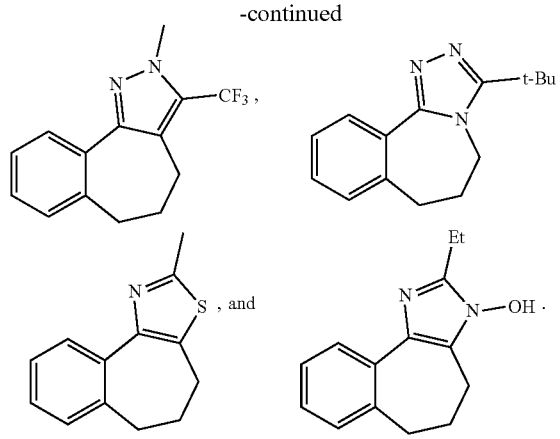
21. The method of claim 14, wherein ligand L is selected from:
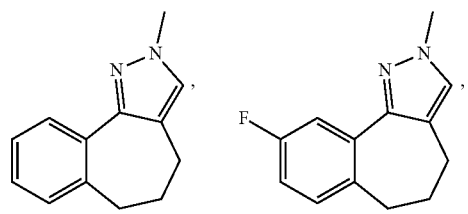
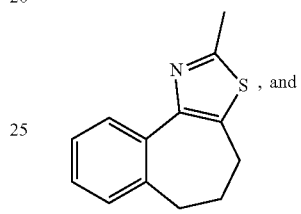
* * * * *